United States Patent [19]
Karasuyama et al.

[11] Patent Number: 6,118,044
[45] Date of Patent: Sep. 12, 2000

[54] TRANSGENIC ANIMAL ALLERGY MODELS AND METHODS FOR THEIR USE

[75] Inventors: Hajime Karasuyama, Tokyo; Hiromichi Yonekawa, Omiya; Choji Taya; Kunie Matsuoka, both of Tokyo, all of Japan

[73] Assignees: Sankyo Company, Limited; The Tokyo Metropolitan Institute of Medical Science, both of Tokyo, Japan

[21] Appl. No.: 09/192,545

[22] Filed: Nov. 13, 1998

[30] Foreign Application Priority Data

Nov. 14, 1997 [JP] Japan .................................. 9-313989

[51] Int. Cl.$^7$ ............................. A01K 67/02; C12Q 1/68; C12N 15/85
[52] U.S. Cl. ........................ 800/3; 800/6; 800/8; 800/21; 800/25; 435/6; 435/69.6; 435/320.1; 435/376
[58] Field of Search .............................. 800/9, 18, 8, 21, 800/3, 13, 14, 25; 435/320.1, 6, 69.6, 371, 355, 455, 475; 536/23.1

[56] References Cited

U.S. PATENT DOCUMENTS 5,625,126  4/1997  Lonberg et al. ........................ 800/18

FOREIGN PATENT DOCUMENTS 649 902A1  4/1995  European Pat. Off. .
WO 93/12227  6/1993  WIPO .
WO 95/17085  6/1995  WIPO .

OTHER PUBLICATIONS

E. Kilchherr, V. Mandak, K. Wagner and C.H. Heusser, "Regulation of Human IgE Response in hu–PBL–SCID Mice", *Cellular Immunology,* 151, 241–256 (1993).

Robert I. Tepper, Douglas A. Levinson, Ben Z. Stanger, Juanita Campos–Torres, Abdul K. Abbas, and Philip Leder, "IL–4 Induces Allergic–like Inflammatory Disease and Alters T Cell Development in Transgenic Mice", *Cell,* 62, 457–467 (1990).

Martin Adamczewski, Georges Köhler and Marinus C. Lamers, "Expression and Biological Effects of High Levels of Serum IgE in ε Heavy Chain Transgenic Mice", *Eur. J. Immunol.,* 21, 617–626 (1991).

Chemical Abstracts Service, Colombus, Ohio, Database Chemabs, Hajime Karasuyama, "A Transgenic Mouse Model of Type I Allergy", AN 129:174353 CA, abstract from *Immunol. Front.,* (1988), 8(4), 231–233.

Flood et al. Immunological signals which control T cell responses, J Endod. 18(9): 435–9, Sep. 1992.

Wilson JM. Animal Modes of Human Diseases for Gene Therapy. J. Clin Invest 98(11): S27–29, 1996.

Rodriquez et al. Expression of active human erythropoietin in the mammary gland of lactating transgenic mice and rabbits Biol Res. 28(2): 141–53, 1995.

Li et at. Sex and tissue–specific expression of a cytochrome P450 2C2–luciferase transgene. Mol Cell Endrocinology. 120(1): 77–83, Jun. 1996.

Mullins et al. Transgenesis in the Rat and Larger Mammals. J Clin Invest. 98(11): S37–40, 1996.

Fung–Leung et al. Transgenic mice expressing the Human High–Affinity IgE receptor . . . J. Exp Med. 183: 49–56, Jan. 1996.

Kofler et al. Mechanism of Allergic Cross–Reactions . . . Mol Immunology. 29(2): 161–66, 1992.

Nikaido et al. Nucleotide sequences . . . J. Biol. Chem. 257: 7322–7329, 1982.

Ishida et al. The nucleotide sequence . . . EMBO J. 1: 1117–1123, 1982

Xiao et al. Genbank110. Accession U65535, Aug. 1996.

Ichikawa et al. Accession W31752, Apr. 1996.

Sun et al. Expression of Human IgE in Transgenic Mice. FASEB. 5(5): A1370, 1991.

*Primary Examiner*—John LeGuyader
*Assistant Examiner*—Carrie Stroup
*Attorney, Agent, or Firm*—Frishauf, Holtz, Goodman, Langer & Chick, P.C.

[57] ABSTRACT

Transgenic mice which constitutively express an antibody–type molecule encoded by the transgene and which has an IgE heavy chain constant region and is specific for a pre–defined antigen, provide an allergic reaction to that antigen without prior sensitization and are useful as allergy models.

11 Claims, 2 Drawing Sheets

TRANSGENIC ANIMAL ALLERGY MODELS AND METHODS FOR THEIR USE

FIELD OF THE INVENTION

The present invention relates to transgenic animals for use in the field of research into allergies, and to methods for their production and use.

BACKGROUND OF THE INVENTION

In order to induce an allergic reaction in an experimental animal, it has conventionally been necessary to first sensitize the animal, by immunizing it repeatedly with the antigen or allergen, prior to administering the antigen or allergen to obtain the desired reaction. Sensitizing large numbers of animals at the same time is not only laborious, but also troublesome, as responsiveness is tends to be variable among individual animals, so that it is difficult to obtain similar results from one experiment to the next.

Recently, the NC/Nga mouse has attracted attention as an animal model for atopic dermatitis. However, the dermatitis developed in this mouse is spontaneous, rather than induced, so that it does not develop as a result of the mouse being exposed to a specific allergen. This is inconvenient when researching cures for allergies. It does not help that the allergen which induces dermatitis in the mouse has not been identified.

Allergic reactions are initiated by the cross-linking of the high affinity immunoglobulin E receptor, FCεRI, present on mast cells, by immunoglobulin E (IgE), once it has specifically bound to the allergen. This binding releases histamines and other mediators and leads to degranulation of the mast cells and, ultimately, the observed allergic response. To date, treatment has typically involved histamine antagonists or steroidal anti-inflammatory drugs. The discovery of more specific treatments is hampered by not having a reliable animal model.

An IgE transgenic mouse was obtained by Adamczewski et al. [Eur. J. Immunol. 21:617–626 (1991)]. The purpose sought to be achieved by this team was to develop an in vivo model system in which high levels of IgE could be achieved without antigenic stimulation. Accordingly, a gene coding for the heavy chain of IgE was introduced into the mouse. It was found that 100-fold higher titers of transgenic IgE were elicited, while levels of native IgE were not affected. Allergic responses also were not affected. The high titers of transgenic IgE were found to temporarily inhibit allergic responses, but it was concluded that, as only very low levels of mast cell binding are required to achieve an allergic response, then it would only require some dissociation of transgenic IgE to trigger a response. Antigen specific IgE was not obtained.

WO 95/15376 discloses humanized transgenic mice in which at least one human gene encoding the α chain of the FCεRI receptor replaces expression of its murine analogue. This is sufficient to allow human IgE to bind the transgenic mast cells and trigger an allergic response. This model suffers in that the animal is not responsive to an antigen, human antibodies having to be administered in order to accomplish testing.

OBJECT OF THE INVENTION

Accordingly, it is an object of the present invention to provide a novel transgenic animal, and a method for using it, that is useful as a reliable animal model for the search for, and/or evaluation of, anti-allergic drugs.

SUMMARY OF THE INVENTION

We have now, surprisingly, found that it is possible to provide such an animal model by altering its genome to constitutively express an antibody-type molecule having an IgE heavy chain constant region or equivalent which can bind the IgE receptor on mast cells, and which is specific for a pre-defined antigen. This may be achieved by using DNA coding for the heavy IgE chain and from which the exons coding for the transmembrane portion have been removed. Thus, the animal will exhibit an allergic reaction after its very first exposure to the antigen for which the IgE is specific, without the need for sensitization.

Thus, in a first aspect, the present invention provides a transgenic, non-human animal characterized in that its genome has been altered to constitutively express a molecule having an immunoglobulin structure comprising:

at least one antigen recognition site comprising an immunoglobulin heavy chain variable region and an immunoglobulin light chain variable region; and a heavy chain constant region enabling the molecule to bind an IgE receptor on mast cells in the animal; the recognition site having specificity for a pre-determined antigen.

In an alternative aspect, there is provided a transgenic, non-human animal characterized in that its genome has been altered to constitutively express an antibody-type molecule having a constant region, preferably an IgE heavy chain constant region or portion or equivalent thereof, which can bind the IgE receptor on mast cells in the animal, the molecule having a pre-determined specificity.

In a further aspect, there is provided a transgenic, non-human animal characterized in that its genome has been altered to constitutively express IgE having a pre-determined specificity.

There is yet further provided a transgenic, non-human animal characterized in that the animal exhibits an allergic reaction after a single administration of a pre-determined antigen, without the necessity for prior sensitization.

DETAILED DESCRIPTION OF THE INVENTION

Figure 1:
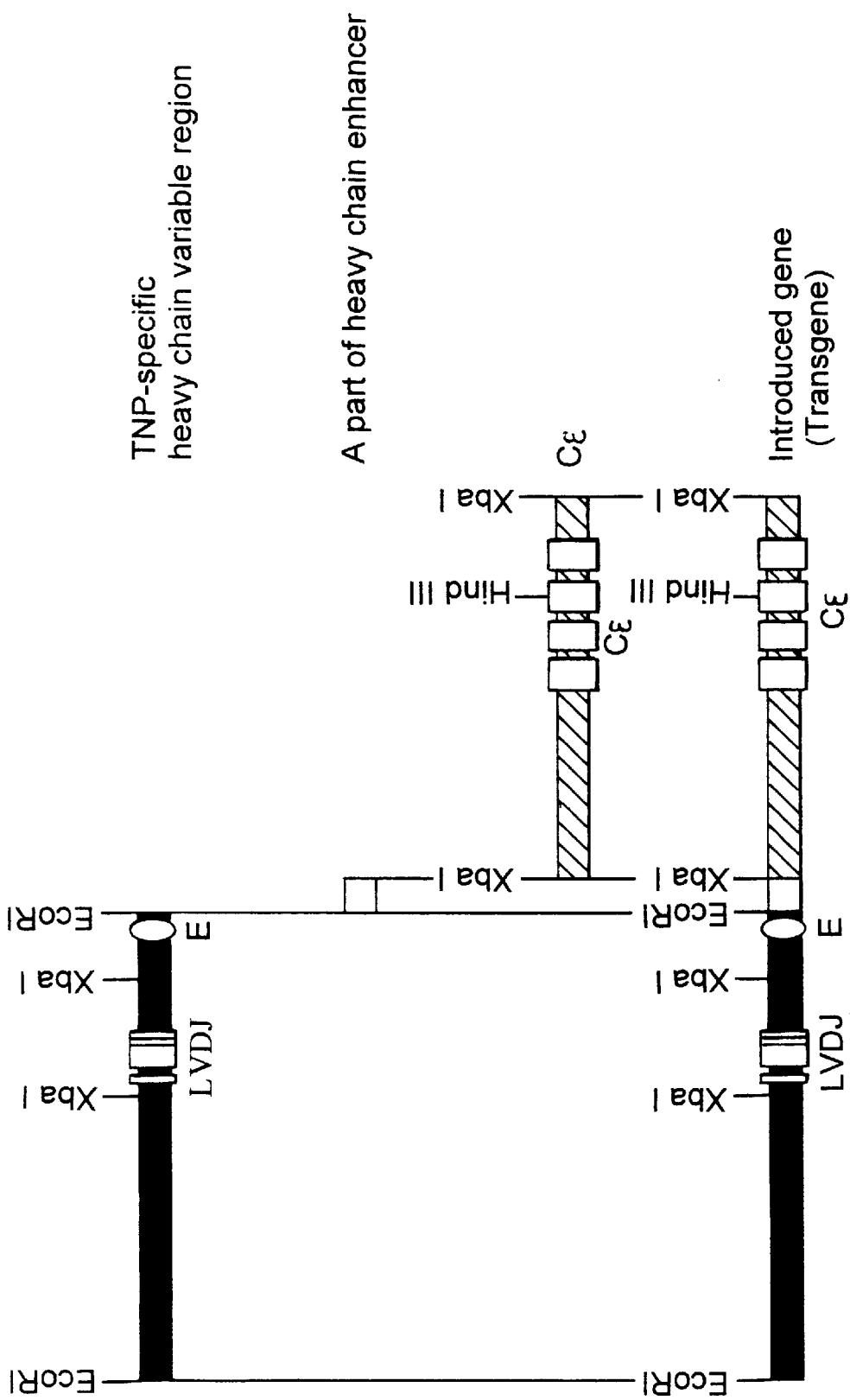
FIG. 1 depicts the construction of a gene for the expression of murine anti-TNP IgE heavy chain in a mouse.

As used herein, "an antibody-type molecule" is a molecule which has specificity for a pre-determined antigen which has the characteristic immunoglobulin structure comprising at least one light and one heavy chain, preferably one of each. There should be at least one heavy chain constant region which is able to bind to an IgE mast cell receptor. This constant region need not be one that occurs in nature, but is suitably derived directly from an appropriate IgE constant region, or may only comprise such amino acid sequences, or equivalents, of the IgE constant region as are necessary for binding the receptor.

By "the equivalent thereof" is meant any suitable sequence or sequences which, when incorporated into the constant region of the transgenic molecule, enables binding to the IgE mast cell receptor in the same or similar manner to that of the appropriate IgE constant region, i.e., which is sufficient to elicit a response from the receptor when cross-linked with the transgenic molecule when complexed with the antigen.

Likewise, the terms "heavy chain variable region" and "light chain variable region" are used to indicate a region of the molecule for antigen binding which has the immunoglobulin antigen recognition type of structure and that, while the regions may usefully be selected from those occurring in nature, engineered domains having the necessary recognition ability may equally be employed.

It will be appreciated that the present invention has the advantage of providing a stable animal model which will react predictably to a given antigen, or antigens, depending on the number of different IgE molecules it has been engineered to express. There is no longer the need for sensitization to the antigen, which could be lengthy and have varying outcomes, including the level of IgE production.

Animals of the present invention generally exhibit substantially consistent levels of transgenic IgE, typically of around 8 μg/ml or higher. In any event, it will also be recognized that the person skilled in the art will readily be able to ascertain the levels of transgenic IgE expressed in any given animal, by methods well known in the art, and such as are described below.

Animals expressing specific IgE, unless suffering from a deficiency of the FCεRI receptor for example, will already be expressing levels IgE generally as high, or higher, than animals which have previously been sensitized to the antigen and, so, will exhibit an allergic response on first exposure to the antigen. This considerably facilitates the search for anti-allergic agents, be they general or specific.

The animals of the present invention exhibit an allergy to a specific antigen, and this can suitably be chosen so that the animal mimics a human allergic condition, such as hay fever or atopic dermatitis, for example. Research can then be performed to find therapies for the specific condition, or the model may be chosen so as to elicit a readily identifiable allergic response, so as to provide an easily measurable marker for use in testing potential, non-specific, anti-allergic therapies.

Specific therapies may concentrate on preventing cells of a certain category expressing IgE, for example, or may bind the specific binding site recognized by the IgE molecule. Non-specific therapies may concentrate on preventing overall expression of IgE, which is potentially dangerous, or may seek to block binding with the FCεRI receptor, for example.

Animals for use in the present invention may be any suitable, provided that they exhibit allergic responses mediated by IgE. Many smaller mammals are convenient to use, and it is particularly desirable that, in the absence of other constraints, they should breed rapidly and be easy to maintain. We prefer that the animal should be a rabbit, rat or mouse, with mice being most preferred.

The animals of the invention express IgE having a predetermined specificity, by which is meant that the transgenic DNA coding for the IgE has been modified such that the resulting IgE will specifically bind a chosen antigen. This can be achieved by obtaining a hybridoma, for example, which expresses a monoclonal antibody specific for the chosen antigen, and then cloning the coding DNA by methods well known in the art.

The advantage of using such DNA is that the internal rearrangements of the variable region have already been made, so that no further rearrangement is possible. When this is inserted into the genome, together with an appropriate promoter and enhancer region, the result is that an IgE sub-unit (heavy or light chain) with a pre-defined specificity will be expressed. It will be appreciated that the gene coding for the transgenic immunoglobulin may be either cDNA or genomic DNA. However, genomic DNA in association with a promoter and enhancer region is preferred.

It will be appreciated that, for best recognition, both the heavy and light chain variable regions should be complementary and recognize the same antigen.

It is also generally preferred that both variable regions come from the same type of antibody molecule, although there is not an especially strong preference for them to originate from IgE. In addition, it is also preferred that the variable regions come from a homogeneous source, such as mouse for mouse, etc., although this not particularly important.

What is necessary is that the transgenic IgE be able to bind the mast cell receptor, typically the FCεRI receptor, expressed in the animal, once the antigen has been complexed. If the animal is a mouse, then the constant region from the heavy chain of murine IgE, or at least that portion (s) necessary for binding FCεRI, or an equivalent thereof, should form part of the transgenic insert, otherwise there may be no binding to FCεRI, even if the antigen is complexed.

Alternatively, and in a preferred embodiment, the constant region from the heavy chain of human IgE, or at least that portion(s) necessary for binding human FCεRI, or the equivalent thereof, is used, and the animal's FCεRI receptor is humanized, such as is described in WO 95/15376, which document is incorporated herein by reference. In such an embodiment, the human IgE constant region may correspond directly to the raised sequences illustrated in FIG. 4B of Flanagan & Rabbitts [EMBO Journal, (1982), 1, No. 5, 655–660, incorporated herein by reference].

Accordingly, it will also be appreciated that the IgE expressed by the animal need not correlate exactly, or even very much, with naturally occurring IgE in the animal in question, provided only that it is capable of binding a pre-determined antigen and that, once so bound, it is capable of cross-linking, or otherwise interacting with, the mast cell receptor and eliciting an allergic response in the transgenic animal.

More specifically, while the gene coding for the heavy or light chain of the antigen specific immunoglobulin may be derived from any animal, it is preferred that the following conditions be satisfied:

1) The constant region of the heavy chain is derived from a secretory IgE molecule (used herein to refer to an IgE molecule having no transmembrane portion and which is extracellularly secreted). The light chain constant region is preferably from an animal of the same species as that from which the heavy chain constant region derives, but is not restricted thereto;

2) The variable regions of the heavy and light chains are derived from the same immunoglobulin molecule and may be from the same parent IgE as that from which the constant region derives; and 3) The heavy chain constant region is able to bind to the IgE receptor expressed in the animal to which the gene is introduced.

The gene or genes coding for the immunoglobulin is preferably derived from rodents, such as mice or rats, or is derived from primates, such as monkeys or humans, more preferably from mice or humans. A particularly preferred genetic sequence is that which encodes a polypeptide comprising the heavy chain constant region which, in turn, comprises the amino acid sequence of SEQ ID No. 2, amino acid Nos. 120 to 542, in the Sequence Listing, together with a heavy chain variable region from any antibody. A particularly preferred DNA encoding a polypeptide comprising the light chain constant region codes for the amino acid sequence as defined by amino acid Nos. 114 to 219 of SEQ ID No. 4 in the Sequence Listing, with a light chain variable region deriving from the antibody having the above heavy chain variable region. More preferably, the DNA encodes a polypeptide comprising the amino acid sequence as defined by amino acid Nos. 1 to 542 of SEQ ID No. 2 in the Sequence Listing and/or DNA coding for the polypeptide comprising the amino acid sequence as defined by amino acid Nos. 1 to 219 of SEQ ID No. 4 in the Sequence Listing.

As stated above, immunoglobulins providing the variable regions may be of any isotype, such as IgG, IgD, IgM, IgA and IgE, regardless of whether they are in a secretory or membrane-bound form. Therefore, immunoglobulins coded by the transgenes of the transgenic animal of the present invention are not limited to a natural form; and may be one in which the variable regions are from IgG and the heavy chain constant region is from IgE, for example, or may be even an artificially modified antibody such as a chimaeric antibody or a humanized antibody.

Provided that a gene product of a gene coding for an immunoglobulin from an animal of a different species or encoding an artificially modified antibody is able to bind either an endogenous or foreign (i.e., genetically modified) IgE receptor expressed in the animal, then there should be no problem. It is unlikely that the immunoglobulin will be recognized as non-self, as the gene encoding the immunoglobulin will normally have been incorporated into the germline of the animal, so that immunological tolerance will be established. Thus, in the absence of the particular antigen, it will not generally affect development or growth of the animal.

The source of the genetic material for the transgenic immunoglobulin may be any that is suitable. For ease, cells producing sufficient amounts of antigen-specific immunoglobulin should be used, particularly hybridomas producing monoclonal antibodies. If it is only desired to obtain genomic DNA coding for the secretory IgE constant region, then other cell types may also be used. For cells producing secretory IgE, hybridomas producing only the desired antigen-specific IgE are preferably used. A suitable example of such an IgE-producing hybridoma is IGEL-b4 [ATCC TIB 141, see Eur. J. Immunol. (1981) 11, 527–529 and Mol. Immunol. (1992) 29, 161–166], which secretes IgE that specifically binds to substances bearing TNP groups ("anti-TNP IgE").

It will be appreciated that it is important for the IgE to be produced constitutively, at least by the time the animals are at the age by which it is required to test them for allergic response. If it becomes necessary to induce production of the antibody, then this adds an extra step to testing, and may make the whole procedure no better than the previously required sensitization. Thus, it is important that the transgenic antibody be continuously expressed at levels sufficient to elicit an immediate allergic reaction, i.e. a reaction will occur as fast, or faster, than in a sensitized normal animal.

The antigen may generally be any with which immunoglobulin (Ig) can specifically bind, and which is not normally produced by the animal of the present invention, whether natural or artificial in origin. Some suitable allergens are exemplified below:

allergens derived from pollen, such as those derived from trees such as Japanese cedar (Cryptomeria, Cryptomeria japonica), grasses (Gramineae), such as orchardgrass (Dactylis, *Dactylis glomerata*), weeds such as ragweed (Ambrosia, *Ambrosia artemisiifolia*); specific examples of pollen allergens including the Japanese cedar pollen allergens Cry j 1 [J. Allergy Clin. Immunol., 71, 77–86 (1983)] and Cry j 2 [FEBS Letters, 239, 329–332 (1988)], and the ragweed allergens Amb a I.1, Amb a I.2, Amb a I.3, Amb a I.4, Amb a II etc.;

allergens derived from fungi (Aspergillus, Candida, Alternaria etc.);

allergens derived from mites (allergens from *Dermatophagoides pteronyssinus, Dermatophagoides farinae* etc.; specific examples of mite allergens including Der p I, Der p II, Der p III, Der p VII, Der f I, Der f II, Der f III, Der f VII etc.;

house dust;

allergens derived from animal skin debris, feces and hair (for example, the feline allergen Fel d I);

allergens derived from insects (such as scaly hair or scale of moths, butterflies, Chironomidae etc., poisons of the Vespidae, such as *Vespa mandarinia*);

food allergens (eggs, milk, meat, seafood, beans, cereals, fruits and vegetables etc.);

allergens derived from parasites (such as roundworm and nematodes, for example anisakis);

drugs (such as penicillin and insulin);

chemical substances (such as isocyanates, ethylene oxide, phthalic anhydride and latex); and 2,4,6-trinitrophenol etc., and substances having one or more trinitrophenyl (TNP) groups.

Preferred allergens are those having one or more TNP groups. Many of the above allergens can be purchased, for example, from Funakoshi, K. K.

The transgenic animals of the present invention may be heterozygous or homozygous for the introduced foreign gene or genes coding for the heavy and or light chains of the immunoglobulin. In either case, the introduced gene will express, so that the animal can be used as an allergic animal model. However, for continuity of supply, when the transgenic animal of the present invention is intended for breeding, whether or not it is also transgenic for another trait, it is better that at least. one of the parents be a homozygous animal of the present invention, in order to ensure that all offspring express the transgenic immunoglobulin.

It will be appreciated that the animals of the present invention can be produced by various means. For example, an animal carrying just a gene for the heavy chain of the transgenic immunoglobulin can be obtained by injecting DNA into the pronuclei of fertilized eggs. At the same time, DNA encoding the light chain might also be injected. Alternatively, once an animal carrying the heavy chain encoding gene has been obtained, it can be cross-bred with an animal carrying the gene for the light chain. As a further option, eggs from either could be micro-manipulated to introduce the missing DNA. Other options will be apparent to those skilled in the art. Thus, although a transgenic animal containing only one gene coding for either of the heavy or light chain of the transgenic immunoglobulin may not be particularly useful in itself, it can be useful in the production of a transgenic animal of the present invention.

Various preferred embodiments of the present invention are as follows:

A transgenic animal characterized in that the animal has, in the somatic cells and germline cells, a gene coding for a heavy immunoglobulin chain wherein the constant region is derived from secretory immunoglobulin E and the variable region is derived from an immunoglobulin-type molecule having specific binding activity to a pre-defined antigen, together with a gene coding for an immunoglobulin light chain having specificity for the same antigen. Preferably, the light chain variable region derives from the same immunoglobulin as the heavy chain variable region.

It is preferred that the pre-defined antigen is selected from the group consisting of pollen-derived allergens, fungus-derived allergens, mite-derived allergens, house dust, allergens of animal origin, allergens of insect origin, food allergens, allergens of parasite origin, drug allergens, chemical substance allergens and particularly substances having one or more trinitrophenyl groups.

The transgenic animal is preferably a rodent, particularly a moose.

It is preferred that the DNA encoding the constant regions of the immunoglobulin chains derives from secretory immunoglobulin E of an animal of the same species as the transgenic animal.

The heavy chain constant region of the secretory immunoglobulin E preferably comprises the amino acid sequence defined by amino acid Nos. 120 to 542 of SEQ ID No. 2 in the Sequence Listing. Preferably the DNA comprises the nucleotide sequence defined by nucleotide Nos. 415 to 1683 of SEQ ID No. 1 in the Sequence Listing.

The gene coding for the light chain constant region of the secretory immunoglobulin E preferably comprises the nucleotide sequence defined by nucleotide Nos. 397 to 714 of SEQ ID No. 3 in the Sequence Listing.

Preferably the heavy and light chain variable regions both derive from immunoglobulin E, preferably from an animal of the same species as the transgenic animal. In this case, it is particularly preferred that the heavy chain of the secretory immunoglobulin E comprises the amino acid sequence defined by amino acid Nos. 1 to 542 of SEQ ID No. 2 in the Sequence Listing and/or, but preferably and, that the light chain of the secretory immunoglobulin E comprises the amino acid sequence defined by amino acid Nos. 1 to 219 of SEQ ID No. 4 in the Sequence Listing.

In this embodiment, it is preferred that the gene coding for the heavy chain of immunoglobulin E is DNA comprising the nucleotide sequence defined by nucleotide Nos. 58 to 412 of SEQ ID No. 1 in the Sequence Listing. It is also preferred that the gene coding for the light chain of immunoglobulin E is DNA comprising the nucleotide sequence defined by nucleotide Nos. 58 to 394 of SEQ ID No. 3 in the Sequence Listing.

A preferred process for producing a transgenic animal of the invention, comprises introducing into a fertilized egg of an animal a) a gene coding for an immunoglobulin heavy chain wherein the constant region is derived from secretory immunoglobulin E and the variable region is derived from an immunoglobulin-type molecule which has specific binding activity for a particular antigen, and b) a gene coding for an immunoglobulin light chain wherein the variable region is derived from the same immunoglobulin as the heavy chain variable region, then c) transferring the fertilized egg to the oviduct of a female animal of the same species that has been treated to induce pseudopregnancy, and d) allowing the egg to develop in the uterus of the animal.

Another preferred process for producing an animal of the invention, comprises mating an animal transgenic for a gene coding for a immunoglobulin heavy chain wherein the constant region is derived from secretory immunoglobulin E and the variable region is derived from immunoglobulin having a specific antigen binding activity with another animal of the same species transgenic for a gene coding for a immunoglobulin light chain wherein the variable region is derived from the same immunoglobulin as the heavy chain variable region, and obtaining an animal having both genes.

There is also provided a process for producing the animal of the invention, comprising producing an animal transgenic for a gene coding for an immunoglobulin heavy chain wherein the constant region is derived from secretory immunoglobulin E and the variable region is derived from immunoglobulin having a specific antigen binding activity, and then producing from the transgenic animal or its offspring an animal transgenic for a gene coding for an immunoglobulin light chain wherein the variable region is derived from the same immunoglobulin as the heavy chain variable region.

There is further provided a process for producing the animal of the invention, comprising producing an animal transgenic for a gene coding for an immunoglobulin light chain wherein the variable region is derived from immunoglobulin having a specific antigen binding activity, and then producing from the transgenic animal or its offspring an animal transgenic for a gene coding for an immunoglobulin heavy chain wherein the constant region is derived from secretory immunoglobulin E and the variable region is derived from immunoglobulin having a specific antigen binding activity.

The invention also provides a process for evaluating the anti-allergic activity of a substance by obtaining a transgenic animal, as defined above, wherein the immunoglobulin is specific for the desired antigen, and applying the substance to the animal in a manner and under conditions which permit evaluation as an anti-allergic agent.

There is also provided a process for evaluating the effects of a substance as an anti-allergic agent, using a transgenic animal as defined above, characterized in that, in a system wherein the antigen that is specifically bound by the immunoglobulin coded by the genes introduced into the animal is administered to the animal to elicit an allergic reaction, the substance being tested is administered to the animal before, after, simultaneously or sequentially with the administration of the antigen, and the magnitude of the allergic reaction elicited in the animal is compared to that elicited in an animal receiving the antigen but not the substance being tested.

It will be appreciated that, where specific sequences are referred to herein, sequences corresponding to those sequences are also contemplated. For example, it will be appreciated that the genetic sequence is redundant, so that, where an amino acid sequence is encoded, for example, there will be many different nucleotide sequences encoding the amino acid sequence. It will also be appreciated that naturally occurring variants, as well as mutations, of sequences occur, without any significant impact on activity, and such sequences are also contemplated.

Any appropriate method may be employed to isolate the target gene from the relevant source, and any of those in conventional gene cloning may be used. Suitable cloning methods are outlined below, but the present.invention is not limited thereby.

Extraction of mRNA can be performed by the guanidinium thiocyanate-hot phenol method or by the guanidinium thiocyanate-guanidinium HCl method, for example, but the guanidinium thiocyanate-cesium chloride method is preferred. Preparation of mRNA from cells is generally performed by first preparing total RNA and then purifying mRNA from the total RNA by using a poly(A)$^+$ RNA purification matrix, such as oligo(dT) cellulose and oligo (dT) latex beads. Alternatively, mRNA may be prepared directly from a cell lysate using such a matrix. Methods for preparing total RNA include: alkaline sucrose density gradient centrifugation [c.f. Dougherty, W. G. and Hiebert, E., (1980), Virology, 101, 466–474]; the guanidinium thiocyanate-phenol method; the guanidinium thiocyanate-trifluorocesium method; the phenol-SDS method; and the method using guanidinium thiocyanate and cesium chloride [c.f. Chirgwin, J. M., et al., (1979), Biochemistry, 18, 5294–5299]. The currently preferred method is that using a total RNA extraction solvent [ISOGEN (registered trademark); Nippon Gene, K. K.].

The thus obtained poly(A)$^+$ RNA can be used as the template in a reverse transcriptase reaction to prepare single-strand cDNA [(ss) cDNA]. The (ss) cDNA obtained by the use of reverse transcriptase, as described above, can then be converted to double stranded (ds) cDNA. Suitable methods for obtaining the ds cDNA include the S1 nuclease method [c.f. Efstratiadis, A., et al.,(1976), Cell, 7, 279–288], the Gubler-Hoffman method [c.f. Gubler, U. and Hoffman, B. J., (1983), Gene, 25, 263–269] and the Okayama-Berg method [c.f. Okayama, H. and Berg, P., (1982), Mol. Cell. Biol. 2, 161–170]. However, the currently preferred method involves the polymerase chain reaction [PCR —c.f. Saiki, R. K., et al., (1988), Science, 239, 487–491] using single-strand cDNA as the template. Thus the preferred procedure is labeled "RT-PCR", as it involves reverse transcription and PCR.

In the case of immunoglobulins, primers for cloning the gene from mouse mRNA by PCR are commercially available for both the heavy and the light chains. Thus, a cDNA fragment coding for the desired immunoglobulin heavy or light chain can easily be obtained by performing RT-PCR using RNA extracted from an appropriate hybridoma together with a ready-made primer.

The ds cDNA obtained above may then be integrated into a cloning vector and the resulting recombinant vector can then be used to transform a suitable micro-organism, such as E. coli. The transformant can be selected using a standard method, such as by selecting for tetracycline resistance or ampicillin resistance encoded by the recombinant vector. If E. coli is used, then transformation may be effected by the Hanahan method [c.f. Hanahan, D. (1983), J. Mol. Biol. 166, 557–580]. Alternatively, the recombinant vector may be introduced into competent cells prepared by co-exposure to calcium chloride and either magnesium chloride or rubidium chloride. If a plasmid is used as a vector, then it is highly desirable that the plasmid harbors a drug-resistant gene, such as mentioned above, in order to facilitate selection. Brute force selection is possible, but not preferred. Although plasmids have been discussed, it will be appreciated that other cloning vehicles, such as lambda phages, may be used.

Various methods are exemplified below for selecting a host strain having cDNA coding for the desired subunit of the antigen-specific immunoglobulin of interest from the resulting transformants. If the cDNA of interest has been specifically amplified by the above mentioned RT-PCR method, then it is possible to omit these steps.

(1) Screening by Polymerase Chain Reaction

If all or part of the amino acid sequence of the desired protein has been elucidated, then sense and antisense oligonucleotide primers corresponding to separate non-contiguous parts of the amino acid sequence can be synthesized. These primers can then be used in the polymerase chain reaction technique [c.f. Saiki, R. K., et al. (1988), Science, 239, 487–491] to amplify the desired DNA fragment coding for the heavy or the light chain subunit of the desired antigen-specific immunoglobulin. The template DNA used herein may be, for example, cDNA synthesized by reverse transcription from the mRNA of a hybridoma producing a TNP antigen-specific monoclonal IgE.

The DNA fragment thus synthesized may either be directly integrated into a plasmid vector, such as by using a commercial kit, or may be labeled with, for example, $^{32}$P, $^{35}$S or biotin, and then used as a probe for colony hybridization or plaque hybridization to obtain the desired clone.

The partial amino acid sequence of each subunit of the antigen specific immunoglobulin, which is to be introduced into the transgenic animal of the present invention, may be determined by methods well known in the art. For example, each subunit may be isolated using electrophoresis, or column chromatography, and then analyzing the N-terminal amino acid sequence of each subunit using an automated protein sequencer, such as the PPSQ-10, Shimadzu Seisakusyo, K. K., which is preferred.

Harvesting of DNA encoding each subunit of the antibody from the appropriate transformants obtained above may be performed by well known techniques, such as those described by Maniatis, T., et al. [in "Molecular Cloning A Laboratory Manual" Cold Spring Harbor Laboratory, NY, (1982), incorporated herein by reference]. For example, the region of DNA coding for the desired subunit may be excised from plasmid DNA after separating the fraction corresponding to the vector DNA from a transformant which has been determined to possess the necessary plasmid.

(2) Screening Using a Synthetic Oligonucleotide Probe

If all or part of the amino acid sequence of the desired protein has been elucidated, then a short contiguous sequence, which is also representative of the desired protein, may be used to construct an oligonucleotide probe. The probe encodes the amino acid sequence but, owing to the degeneracy of the genetic code, there may be a large number of probes that can be prepared. Thus, an amino acid sequence will normally be selected which can only be encoded by a limited number of oligonucleotides. The number of oligonucleotides which it is necessary to produce can be further reduced by the substitution of inosine where any of the four normal bases can be used. The probe is then suitably labeled, such as with $^{32}$P, $^{35}$S or biotin, and is then hybridized with denatured, transformed DNA from the transformant which has been immobilized on a nitrocellulose filter. Positive strains show up by detection of the label on the probe.

Wherever appropriate, DNA sequences may be sequenced by various well known methods in the art including, for example, the Maxam-Gilbert chemical modification technique [c.f. Maxam, A. M. and Gilbert, W. (1980) in "Methods in Enzymology" 65, 499–276] and the dideoxy chain termination method using M13 phage [c.f. Messing, J. and Vieira, J. (1982), Gene, 19, 269–276]. In recent years, a further method for sequencing DNA has gained wide acceptance, and involves the use of a fluorogenic dye in place of the conventional radioisotope in the dideoxy method. The whole process is computerized, including the reading of the nucleotide sequence after electrophoresis. Suitable machinery for the process is, for example, the Perkin-Elmer Sequence robot "CATALYST 800" and the Perkin-Elmer model 373 DNA Sequencer. The use of this technique renders the determination of DNA nucleotide sequences both efficient and safe.

By using techniques such as those described above, determination of the DNA sequence can be performed efficiently and safely. Based on the data of the thus determined respective nucleotide sequences of the DNA of the present invention and the respective N-terminal amino acid sequences of the heavy and light chains, the entire amino acid sequences of the heavy and light chains of the antibody to be introduced into the transgenic animal of the present invention can be determined.

If the target gene is to be obtained from genomic DNA, then the desired clone may be isolated by a method similar to that for obtaining cDNA, as above, after the DNA has been extracted by conventional techniques from the cellular gene source and a genomic library has been constructed.

For the constant region of IgE for which the complete, or partial, amino acid sequence is known, DNA coding for the constant region can be separately cloned, based on the sequence information. Thus, in the present invention, the DNA to be introduced may be prepared by ligating the genetic sequence coding for the IgE constant region to a sequence coding for the variable region of the antigen specific Ig. In such a case, if the ligated sequences are both genomic DNA containing introns, then an enhancer sequence may be inserted between them, so that adjusting the reading frames for translation is not necessary. It will be appreciated that, by replacing the sequence coding for the variable region with that from another antigen specific immunoglobulin, it is possible to construct a gene to obtain an allergy animal model against the desired antigen.

Typically, one or more regulatory sequences for the expression of the transgenic immunoglobulin will be incorporated with the transgenic DNA. Any suitable regulatory sequence, such as a promoter and enhancer for expressing the introduced DNA in animal cells may be used, provided that it is functional in the cells of the transgenic animal, promoters and enhancers of immunoglobulin genes being particularly preferred. Suitable promoters and enhancers may be incorporated by ligating a known sequence [c.f., Hiramatsu, R. et al. (1995), Cell, 83, 1113–1123], that has been separately cloned, with the sequence to be introduced, or by using those contained within the cloned DNA.

Suitable genetic material, for introduction into a fertilized animal egg, may be in the form of a genetic fragment comprising DNA coding for immunoglobulin, and a promoter or enhancer that controls the expression of the gene; other portions may be removed, or added, as desired. A vector for amplifying the introduced genetic sequence(s) may be any known cloning vector, with those having suitable restriction sites for excising a fragment necessary for transformation being preferred. Should a vector having no suitable restriction site be used, amplification of just the necessary portion is generally possible by performing PCR using sense and antisense primers corresponding to the two ends of the portion for introduction.

Suitable prokaryotic host cells include, for example, *E. coli* (*Escherichia coli*) and *Bacillus subtilis*. In order to express the gene of interest in such host cells, these host cells may be transformed with a plasmid vector containing a replicon derived from a species compatible with the host, typically having an origin of replication and a promoter sequence, such as lac UV5. These vectors preferably have sequences capable of conferring a selection phenotype on the transformed cell.

A suitable strain of *E. coli* is strain JM109 derived from *E. coli* K12. Suitable vectors include pBR322 and the pUC series plasmids. Suitable promoters include the lactose promoter (lac), the tryptophan lactose promoter (trc), the tryptophan (trp) promoter, the lipoprotein (lpp) promoter, the lambda (λ) PL promoter derived from bacteriophage λ, and the polypeptide chain elongation factor Tu (tufB) promoter.

In general, it will be appreciated that the present invention is not limited to the use of such hosts, vectors, promoters, etc., as exemplified herein and that any suitable systems may be used, as desired.

A suitable preferred strain of *Bacillus subtilis* is strain 207-25, and a preferred vector is pTUB228 [c.f. Ohmura, K., et. al., (1984), J. Biochem., 95, 87–93]. A suitable promoter is the regulatory sequence of the Bacillus subtilis α-amylase gene. If desired, the DNA sequence encoding the signal peptide sequence of α-amylase may be linked to the DNA of the present invention to enable extracellular secretion.

In order to obtain a sufficient amount of the transgene, the sequence(s) may be ligated downstream to a promoter, and adding an enhancer or a poly(A) addition signal sequence etc. as necessary, and then subcloning the resulting construct into an amplification vector to provide a recombinant vector and, thereafter, amplifying the vector by culturing the host transformed thereby. To increase the efficiency of introduction, the sequence to be introduced is preferably purified by a procedure, such as cesium chloride density gradient centrifugation, after removing the vector fragment by restriction enzyme digestion.

The procedure for obtaining a fertilized egg from an animal, introducing a transgene, implanting the egg into a pseudopregnant animal and making the egg develop, is suitably performed by an established method, such as that of the Hassei Kogaku Jikken Manual (Developmental engineering experimentation manual), Tatsuji Nomura (general ed.), Motoya Katsuki (ed.), 1987; or "Manipulating the Mouse Embryo, A Laboratory Manual," B. Hogan, F. Costantini and E. Lacy, translated by Kazuya Yamauchi, Yutaka Toyota, Tsuneatsu Mori and Yoichiro Iwakura, 1989; or the Official Gazette of Japanese Provisional Publication No. 5-48093, for example.

For example, with mice, female mice (such as BALB/c, C57BL/6) are given an ovulation-inducing agent and then placed with males of the same strain to mate. On the next day, fertilized eggs in the pronuclear stage are removed from the oviducts of the female mice. Then, a solution of the DNA fragment to be introduced is injected into the pronuclei of the fertilized eggs, using a glass microcapillary. In this step, a mixture of both the sequence coding for the heavy chain and the sequence coding for the light chain is preferably injected, although, as stated above, individual transformation is also contemplated. The injected, fertilized eggs are then transferred to the oviducts of pseudopregnant foster mother mice (for example, Slc:ICR) and the young are then born, after about 20 days, generally by spontaneous delivery or cesarean section.

Methods for confirming that the offspring thus obtained carries the transgene are well known, and include, for example: extracting DNA from the tail of the animal and conducting PCR using sense and antisense primers specific to the transgene with the DNA as the template; and Southern blot analysis in which the DNA, after digestion with several restriction enzymes, is subjected to gel electrophoresis, the DNA in the gel being blotted onto a nitrocellulose or nylon membrane, with the membrane being probed with all or a portion of the labeled transgene.

Suitable methods for confirming whether the introduced transgene is actually expressed, in vivo, include enzyme-linked immunosorbent assay (ELISA), for verifying higher blood immunoglobulin levels than in normal animals by measuring immunoglobulin concentration in peripheral blood, as well as ELISA in which the antigen specifically bound by transgenic immunoglobulin is immobilized, to evaluate the binding activity of blood immunoglobulin on the immobilized antigen.

Suitable methods for confirming that the transgenic animal of the present invention produces the required allergic reactions after a first, single administration of the chosen antigen, will be readily apparent to those skilled in the art. For example, the allergic reaction may be ascertained by applying the antigen to the animal's skin and observing whether there is any reddening or swelling of the skin at the application site, or whether systemic anaphylactic symptoms (dyspnoea, decrease in body temperature, loss of motions, increase in permeability of blood vessels and so on) occur after intravenous injection of the antigen.

By testing whether allergic reactions are mitigated by administering a candidate agent for an anti-allergic drug, both before and after antigen administration, or even by co-administration or sequential administration of the potential agent with the antigen, the effectiveness of the agent as the drug can be evaluated. Most of the allergic reactions resulting from administration of the antigen to the transgenic animal of the present invention are classified into type I allergic reactions so that, once a promising candidate has been found, it may be further evaluated in other experimental systems in which type I allergic reactions. Type I allergic reactions are those which are mediated by IgE and is defined as acute inflammation mediated by IgE and mast cell/basophil products such as histamine and arichidonate products.

It will also be appreciated that it is possible to obtain a transgenic animal having various different traits by mating an animal of the present invention, which only has the transgenic IgE, with another strain of transgenic animal from the same species having a different transgenic trait or traits. For example, a transgenic mouse, in which the constant region of the heavy chain of immunoglobulin coded by the transgene is derived from human IgE, may be produced by methodology as described herein [c.f. Seno, M., et al. (1983), Nuc. Acids. Res. 11, 719–726, and Ueda, S. et al. (1982), EMBO J. 1, 1539–1544, both of which disclose the sequence coding for the human IgE constant region] and mated with a transgenic mouse to which a gene coding for the human IgE receptor has been introduced [c.f. Flanagan & Rabbitts, supra; Fung-Leung, W-P. et al. (1996), J. Ex. Med., 183, 49–56 and Dombrowicz, D. et al. (1996), J. Immunol. 157, 1645–1651] to produce a transgenic mouse in which the IgE—IgE receptor system is of the human type, which is particularly useful as an animal model mimicking human allergy.

The present invention is further illustrated by the working and test Examples below, but is not limited thereby. Unless otherwise indicated, basic procedures in gene manipulation were performed in accordance with the procedures well known in the art, and particularly as described, for example, in "Molecular Cloning: A Laboratory Manual", Cold Spring Harbor Laboratory, NY, Maniatis, T., et al. (1982), incorporated herein by reference. All solutions were made up in deionized water, unless otherwise stated.

EXAMPLE 1

Isolation of cDNA Fragments Coding for the Heavy and Light Chains of Anti-TNP IgE (1) Preparation of RNA The anti-TNP IgE producing hybridoma IGEL-b4 [ATCC TIB 141, see Rudolph, A. K. et al. (1981) Eur. J. Immunol., 11, 527–529; Kofler, H. et al. (1992) Mol. Immunol., 29, 161–166; and Naito, K. et al. (1995) Eur. J. Immunol., 25, 1631–1637] was cultured to $5 \times 10^7$ cells in RPMI1640 culture medium (Gibco BRL) supplemented with 5% w/w fetal calf serum, 100 U/ml penicillin-streptomycin, 2 mM L-glutamine and 50 $\mu$M 2-mercaptoethanol at 37° C. in a $CO_2$ incubator. The cultured cells were then centrifuged at 12,000 r.p.m. for 5 minutes to obtain a cell pellet. Then, 1 ml of a total RNA extraction solvent [ISOGEN (registered trademark); Nippon Gene, K. K.] was added to the cell pellet and thoroughly mixed to lyse the cells. Next, 0.4 ml of chloroform was added, with mixing, to the lysate and the aqueous (upper) layer was recovered by centrifugation at 15,000 r.p.m., 4° C., for 15 minutes. An equal volume of 2-propanol was then added to this aqueous fraction and the mixture was chilled at −80° C. for 1 hour. Thereafter, the mixture was centrifuged at 15,000 r.p.m., 4° C. for 20 minutes, and the supernatant was discarded. The precipitate was washed with 1 ml of 75% aqueous ethanol, and again centrifuged at 15,000 r.p.m., for 5 minutes at 4° C. and the supernatant discarded. The pellet was air-dried and then dissolved in 200 $\mu$l of water to form the total RNA sample.

(2) RT-PCR

Using the total RNA sample prepared in (1) above as the template, reverse transcription polymerase chain reaction (RT-PCR) was performed using: a commercially available RT-PCR kit (Gibco BRL); primers specific to mouse immunoglobulin variable regions (either primers 1 and 2 for the heavy chain, or a primer mixture for the light chain; Pharmacia); and Taq polymerase [Ex Taq (registered trademark); Takara Syuzo, K. K.].

Reverse transcription was performed with the following ingredients and methodology:

| | |
|---|---|
| total RNA | 10 to 15 $\mu$g |
| oligo dT (10 $\mu$M; from the kit) | 1 $\mu$l |
| 5 × first strand synthesis buffer (from the kit) | 4 $\mu$l |
| 25 mM magnesium chloride (from the kit) | 2 $\mu$l |
| 0.1 M dithiothreitol (from the kit) | 2 $\mu$l |

Prior to PCR, the template sample was mixed with the above reagents and water was added to a total volume of 19 $\mu$l. After the addition of 1 $\mu$l of reverse transcriptase (from the kit), the mixture was incubated at 42° C. for 50 minutes. PCR (reactions for the heavy chain and for the light chain were conducted separately):

| | |
|---|---|
| reverse transcription solution | 2 $\mu$l |
| 10 × PCR buffer (from the kit) | 5 $\mu$l |
| 10 mM dNTP | 1 $\mu$l |
| primers | |
| heavy chain primers 1 and 2 | 0.5 $\mu$l each |
| light chain primer mixture | 0.5 $\mu$l |

The reverse transcribed sample was mixed with the above reagents and water was added to a total volume of 49.5 $\mu$l. Then, 0.5 $\mu$l of Taq polymerase was added to the mixture which was subsequently incubated at 96° C. for 2 minutes, followed by a thermal cycle of 96° C. for 30 seconds, 55° C. for 1 minute and 72° C. for 1 minute, repeated 40 times, with a final cycle of 72° C. for 7 minutes and 25° C. for 10 minutes.

(3) Isolation of PCR Product

Each of the heavy and light chain RT-PCR reaction products obtained in (2) above was subjected to 0.8% w/v agarose gel electrophoresis. After electrophoresis, the gels were stained with ethidium bromide in accordance with standard practices. The DNA bands were visualized on a UV transilluminator and the gel containing the band corresponding to 300–350 bp for each sample was excised and transferred into a seamless, cellulose dialysis tube to trap eluted DNA. The dialysis tube was then electrophoresed at 100 V for one hour in electrophoresis apparatus (Bio-Craft, Model BE-560) to elute DNA from the gel. After this time, the inner solution in the tube was recovered, extracted respectively first with phenol, then a 50/50 (v/v) mix of phenol/chloroform and, finally, chloroform, and the DNA was precipitated with pure ethanol.

The purified DNA thus obtained was dissolved in 10 μl of TE buffer [10 mM Tris-HCl (pH 8.0), 1 mM ethylenediamine-tetraacetic acid (EDTA)]. The PCR product in the resulting solution was ligated with the plasmid vector pCR II (Invitrogen) using a ligation kit (Takara Syuzo, K. K.). Competent *E. coli* strain JM109, purchased from Nippon Gene, was then transformed by electroporation [Neumann, E., et al. (1982) EMBO J., 1, 841–845] to select ampicillin resistant clones. Resistant clones were cultured on a small scale to prepare plasmid DNA and the sequences thereof were analyzed by the dideoxy method. Accordingly, it was established that clones for the heavy and light chains had been obtained and that they had DNA coding for a portion of the heavy or light chain variable region, as appropriate, of anti-TNP IgE, as produced by IGEL-b4 (nucleotide Nos. 58 to 412 of SEQ ID No.1 and nucleotide Nos. 58 to 393 of SEQ ID No.3 in the Sequence Listing).

(4) Labeling of Probes

Plasmids containing DNA coding either for a portion of the variable region of the heavy chain or a portion of the variable region of the light chain, as obtained in (3) above, were respectively digested with the restriction enzyme EcoRI, subjected to 0.8% w/v electrophoresis, and then each of the insert DNA fragments was isolated by similar methodology to that employed in (3) above. These fragments were respectively labeled with [α-$^{32}$P] dCTP (New England Nuclear (NEN)) using a DNA labeling kit for random primer generation (Version 2; Takara Syuzo, K. K.) to prepare probes for genomic DNA screening.

EXAMPLE 2

Cloning of Genomic DNA Coding for the Heavy and Light Chains of Anti-TNP IgE (1) Extraction of Genomic DNA The anti-TNP IgE producing hybridoma IGEL-b4 was cultured to 1×10$^7$ cells and then centrifuged at 12,000 r.p.m. for 5 minutes. The supernatant was then discarded. The cells in the pellet were washed twice with ice-cold Dulbecco's PBS (−) [phosphate buffered saline (PBS) without calcium or magnesium]. The washed cells were then suspended in 1 ml of 10 mM Tris-HCl buffer (pH 8.0) containing 100 mM NaCl, 25 mM EDTA, 0.5% w/v sodium lauryl sulfate (SDS) and 0.1 mg/ml protease K, and subsequently incubated at 50° C. overnight with shaking. The following day, the mixture was respectively extracted with first phenol, then phenol/chloroform and, finally, chloroform, and the washed mixture was then subjected to ethanol precipitation to purify DNA. The resulting DNA was dissolved in water to provide each of the two genomic DNA samples.

(2) Construction of Genomic Library

The genomic DNA prepared in (1) above was prepared as a number of samples, each was digested with a restriction enzyme selected from EcoRI, BamHI, PstI, Bgl II, XbaI, Hind III and SacI. Each digested sample was subjected to 0.8% w/v agarose gel electrophoresis and then blotted onto a nylon membrane (Hybond-N+; Amersham). Each resulting membrane was hybridized with the probes for the heavy and light chains prepared in Example 1(4) above, as appropriate, a labeled probe of the Hind III-XbaI fragment derived from the plasmid pVH167μ [c.f. Kim, S. et al. (1981) Cell 27, 573–581; Proc. Natl. Acad. Sci. USA (1980) 77, 7400–7404] carrying DNA coding for the heavy chain of mouse IgM, and a labeled Sacd-Sac II fragment of the plasmid pV167Cκ [c.f. Selsing, E. and Storb, U. (1981) Cell 25, 47–58] carrying DNA coding for the mouse IgM light chain.

The Hind III-XbaI fragment of pVH167μ and the SacI-Sac II fragment of pV167Cκ correspond to portions of introns downstream of the variable regions of genomic DNA coding for the IgM heavy and light chains, respectively. A DNA library was prepared for each of the heavy and light chains corresponding to the 300–350 bp band of Example 1(3). In the case of the heavy chain, clones were selected which were detected by both the heavy chain probe prepared in Example 1(4) and by the Hind III-XbaI probe from pVH167μ. In the case of the light chain, clones were selected which were detected by both the light chain probe prepared in Example 1(4) and by the SacI-Sac II probe from pV167Cκ.

To start, the genomic DNA prepared in (1) above was digested with the restriction enzyme EcoRI (in the case of the heavy chain clone) or Hind III (in the case of the light chain clone). Each of the digested samples was then electrophoresed on 0.8% w/v agarose gel, after which the gel was stained with ethidium bromide. Using a UV transilluminator, that part of the gel holding the band of interest was excised and the DNA in the gel was recovered and purified as described in Example 1(3).

The EcoRI fragment (heavy chain), thus obtained, was ligated into λgt10 (Stratagene) while the Hind III fragment (light chain) was ligated into ZAP Express vector (Stratagene), each using T4 DNA ligase (New England Biolabs). The resulting recombinant plasmids were packaged into phages using a packaging kit (GIGAPACK II Gold; Stratagene). Accordingly, DNA libraries having titers of 9×10$^5$ plaque forming units (pfu) (heavy chain library) and 4×10$^6$ pfu (light chain library) were obtained.

(3) Screening

The heavy chain and light chain DNA libraries obtained in the above section (2) were screened for clones hybridizing to the probes prepared in Example 1(4) using the method described below (plaque hybridization).

First, host *E. coli* (for the heavy chain: strain NMS514, for the light chain: strain XL1-Blue MRF'; both from Stratagene) was infected with the appropriate DNA library and cultured to produce 1×10$^5$ plaques on an agar plate prepared in a 15 cm diameter plastic petridish. A nylon membrane (Hybond N+; Amersham) was placed over the plate and allowed to absorb DNA, after which the membrane was removed and air-dried. Next, the membrane was soaked in 0.5 N aqueous NaOH solution containing 1.5 M NaCl, for 5 minutes, to denature DNA on the membrane by the action of the alkali. After this time, the membrane was neutralized in 0.5 M Tris-HCl buffer (pH 7.6) containing 1.5 M NaCl, for 5 minutes. The membrane was further soaked in 2×SSC (1×SSC:—0.15 M NaCl, 15 mM trisodium citrate), for 5 minutes, and then air-dried. DNA was then immobilized on the membrane using UV cross-linker (Stratagene).

Next, the membrane was soaked in a prehybridization solution [50% w/v formamide, 5×SSC, 50 mM sodium phosphate buffer (pH 6.8), 1×Denhardt's solution, and 250 μg/ml denatured salmon sperm DNA] and incubated at 42° C. for 1 hour. After this time, the membrane was incubated in a hybridization solution [a 4:1 (v/v) mix of prehybridization solution and 50% w/v dextran sulfate solution] containing 50 ng of the heavy chain or light chain probe as prepared in Example 1(4), at 42° C., overnight. The membrane was then recovered and washed twice with 2×SSC/0.1% w/v SDS (the first wash for 5 minutes at room temperature and the second for 30 minutes at 50° C.), followed by washing twice with 0.2×SSC/0.1% w/v SDS (each for 30 minutes at 50° C.). After washing, the membrane was air-dried and analyzed by autoradiography using X-ray films (X-OMAT AR; Kodak). Based on the results, the portion of agar containing positive plaques was excised. Phage was recovered from the agar and a single clone was obtained by performing plaque hybridization again at low plaque density.

(4) Cloninc

1) Heavy Chain

Phage DNA was purified (Maniatis et al., ibid.) from the positive clone isolated from the heavy chain library in (3) above, digested with EcoRI, and subjected to 0.8% w/v agarose gel electrophoresis to separate and purify the EcoRI—EcoRI fragment containing the DNA of interest (about 4 kbp). The fragment was cloned into the commercially available pBluescript SK(+) vector which had previously been digested with EcoRI.

2) Light Chain

As the DNA of interest carried in the positive clone isolated from the light chain library (Hind III—Hind III fragment, about 2.5 kbp) had been cloned using the ZAP Express vector system, it was possible for the fragment to be cloned into plasmid pBK-CMV (Stratagene) using a helper phage according to the protocol included with the ZAP Express vector kit.

(5) Verification of Nucleotide Sequences

1) Heavy Chain

The EcoRI—EcoRI fragment obtained in (4) above was further digested with Xba I and separated by 0.8% w/v agarose gel electrophoresis. The EcoRI-Xba I, Xba I—Xba I, and Xba I-EcoRI fragments recovered after electrophoresis were respectively sub-cloned into the pBluescript SK(+) vector. Nucleotide sequence analysis was performed on the resulting clones, and it was verified that the same nucleotide sequence as the heavy chain RT-PCR product was obtained (nucleotide Nos. 58 to 412 of SEQ ID No. 1 in the Sequence Listing).

2) Light Chain

The light chain clone obtained in the section (4) above was digested with Hind III, and the resulting Hind III—Hind III fragment (2.5 kbp) was further digested with Hae III. The fragments recovered after separation by 0.8% w/v agarose gel electrophoresis were sub-cloned into the pBluescript SK(+) vector. Nucleotide sequence analysis was performed on the resulting clones, and it was verified that the light chain clone contained the same nucleotide sequence as the light chain RT-PCR product (nucleotide Nos. 58 to 394 of SEQ ID No. 3 in the Sequence Listing).

EXAMPLE 3

Preparation of Genes to be Introduced

Figure 2:
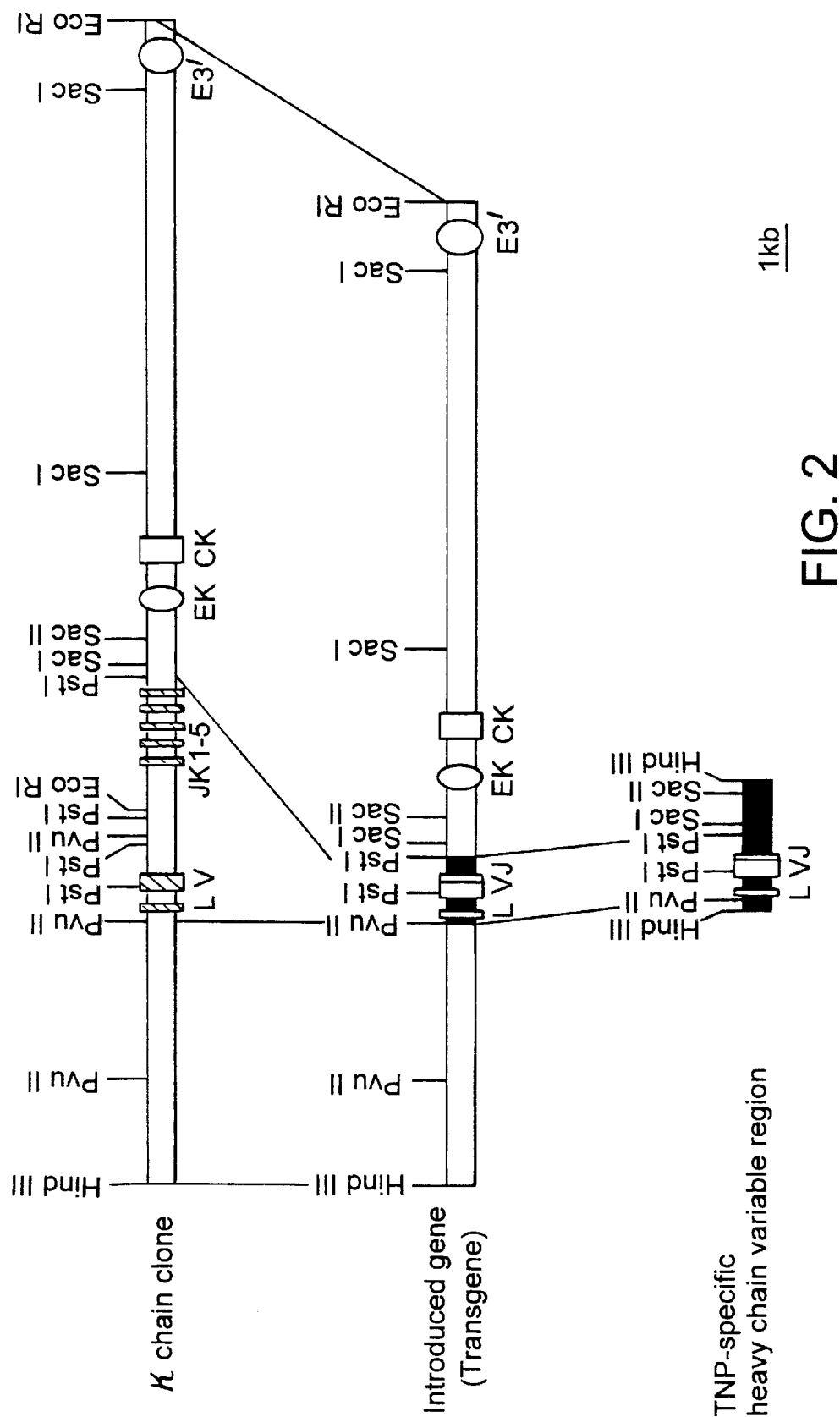
FIG. 2 depicts the construction of a gene for the expression of murine anti-TNP IgE light chain.

The method of construction of each of the transgenes of this Example are outlined in FIGS. 1 and 2.

(1) Treatment of Heavy Chain/Light Chain Genomic DNA

The EcoRI—EcoRI fragment (about 4 kbp) in the heavy chain clone obtained in Example 2(4) above was used directly for the following process, since it contained a promoter and the correct rearranged variable region (VDJ). The Hind III—Hind III fragment (about 2.5 kbp) in the light chain clone obtained in Example 2(4) above was digested with the restriction enzymes Pvu II and Pst I to recover the Pvu II-Pst I fragment (1.5 kbp) containing the correct rearranged variable region (VJ) for use in the following process.

(2) Cloning of Heavy Chain/Light Chain Constant Region Genomic DNA and Promoter-Enhancer 1) Preparation of BALB/c Mouse Genomic DNA library To clone DNA coding for the heavy chain constant region of mouse IgE, a genomic library was constructed as follows.

The liver from a BALB/c mouse (Nippon SLC) was removed and frozen in liquid nitrogen. The frozen liver was then crushed with a hammer and the genomic DNA was extracted and purified in a manner similar to that of Example 2(1) above. DNA coding for the constant region of mouse secretory IgE is known to be located within one of the Xba I—Xba I digested fragments (about 4 kbp) of the genome [c.f. Ishida, N. et al. (1982) EMBO J. 1, 1117–1123]. Accordingly, the purified genomic DNA was digested with Xba I, separated using 0.8% w/v agarose gel electrophoresis and ethidium bromide staining, and that part of the gel containing fragments of between about 2.5 and 4.5 kbp length was excised to recover target DNA. Thereafter, a ZAP Express vector genomic library was constructed in a manner similar to that described in Example 2(2) above.

2) Preparation of Screening Probe

Oligonucleotide primers having the following nucleotide sequences:

5'-CTCAACATCA CTGAGCAGCA ATGG-3'
(sense primer: SEQ ID No. 9 in the Sequence Listing); and
5'-GCGTTATTGT GGTGCTTAGT GTACC-3'
(antisense primer: SEQ ID No. 10 in the Sequence Listing) were synthesized by the phosphoamidite method. Then, using as the template the Xba I—Xba I digested fragment mixture (2.5 to 4.5 kbp) of BALB/c mouse genomic DNA prepared in section 1) above, PCR was conducted under the following conditions.

Composition of the Reaction Solution:

| template DNA | 5 µg |
| sense primer (1 µM) | 5 µl |
| antisense primer (1 µM) | 5 µl |
| 10 × Ex Taq buffer | 10 µl |
| 10 mM dNTP | 10 µl |

Water was added to a total volume of 99 µl, after which 1 µl of Ex Taq polymerase was added to the mixture.

Thermal Treatment:

The PCR mixture was then incubated at 96° C. for 2 minutes, after which a cycle of 96° C. for 30 seconds, 55° C. for 30 seconds, and 72° C. for 1 minute was repeated 30 times, followed by a last cycle of 72° C. for 7 minutes and 25° C. for 10 minutes.

The resulting, amplified 375 bp DNA fragment was cloned into the pCR II vector by a method similar to that described in Example 1(3) above and labeled with $^{32}P$ by a similar method to that described in Example 1(4) above.

3) Screening

Using the probe prepared in 2) above, the genomic library prepared in section 1) above was subjected to plaque hybridization for screening, in a manner similar to that described in Example 2(3) above. The resulting clone (recovered in a form integrated in the plasmid pBK-CMV) was digested with Xba I and subjected to 0.8% w/v agarose gel electrophoresis to recover an Xba I—Xba I fragment of about 4 kbp.

4) Cloning of a Portion of Heavy Chain Enhancer

By reference to known nucleotide sequences of mouse immunoglobulin heavy chain enhancers, oligonucleotide primers having the following nucleotide sequences:
5'-TAGAATTCAT TTTCAAAATT AGG-3'
(sense primer: SEQ ID No. 11 in the Sequence Listing); and
5'-AGTCTAGATA ATTGCATTCA TTTAA-3'
(antisense primer: SEQ ID No. 12 in the Sequence Listing) were synthesized by the phosphoamidite method. Then, using as the template the BALB/c mouse genomic DNA prepared in section 1) above, PCR was conducted under the following conditions.

Composition of the Reaction Solution:

| template DNA | 5 µg |
|---|---|
| sense primer (1 µM) | 5 µl |
| antisense primer (1 µM) | 5 µl |
| 10 × Ex Taq buffer | 10 µl |
| 10 mM dNTP | 10 µl |

Water was added to a total volume of 99 µl, after which 1 µl of Ex Taq polymerase was added.

Thermal Conditions:

The PCR mix was first incubated at 96° C. for 2 minutes, and then a cycle of 96° C. for 30 seconds, 45° C. for 1 minute, and 72° C. for 1 minute was repeated 30 times, followed by a final incubation at 72° C. for 7 minutes.

The resulting reaction solution after PCR was subjected to 0.8% w/v agarose gel electrophoresis and ethidium bromide staining. The purified, amplified DNA fragment was digested with EcoRI and Xba I and again subjected to 0.8% w/v agarose gel electrophoresis to recover a fragment of about 300 bp.

5) Light Chain

In order to obtain genomic DNA coding for the light chain constant region of mouse IgE, the Pst I-Not I fragment (about 12 kbp) was isolated by digesting the DNA clone pMM222 [c.f. Hiramatsu, R. et al. (1995) Cell, 83, 1113–1123]. This fragment contains an intron enhancer, a segment coding for the constant region (Cκ) of mouse IgE and a 3'-terminal enhancer coding for the IgK light chain. By digesting this fragment with the restriction enzymes Pst I and Not I, and by 0.8% w/v agarose gel electrophoresis, DNA coding for the light chain constant region of mouse IgE was obtained. The Sal I-Pvu II fragment (about 5 kbp), containing a promoter, was also isolated from pMM222 by digestion with the restriction enzymes Sal I and Pvu II and purified by 0.8% w/v agarose gel electrophoresis.

(3) Ligation of Variable Region, Constant Region, Promoter and Enhancer

1) Heavy Chain

The EcoRI-Xba I fragment (about 300 bp) containing a portion of enhancer [prepared in section (2) 4) above] was sub-cloned into a pBluescript SK(+) vector which had previously been digested with EcoRI and Xba I. The resulting plasmid was linearized by digestion with Xba I, and then the Xba I—Xba I fragment (about 4 kbp) containing the gene coding for the heavy chain constant region of mouse IgE [prepared in section (2) 3) above] was ligated into it using T4 DNA ligase.

The nucleotide sequence of the resulting clone was analyzed to select a clone carrying the Xba I—Xba I fragment ligated in the correct orientation (i.e., wherein the 5'-end of the sense strand of DNA coding for the constant region was ligated to the 3'-end of the enhancer). The selected clone was then linearized, once more, by EcoRI digestion and the EcoRI—EcoRI fragment (about 4 kbp, containing a promoter and the variable region) from the heavy chain clone obtained in Example 2(4) above was inserted into it by ligation with T4 DNA ligase. The nucleotide sequence of the resulting clone was analyzed to select a clone carrying the EcoRI—EcoRI fragment ligated in the correct orientation (i.e., wherein the 3'-end of the sense strand of DNA coding for the variable region was ligated to the 5'-end of the enhancer).

The resulting, recombinant plasmid contained DNA which included a gene coding for the amino acid sequence (including the leader sequence) as defined in SEQ. ID No. 2 of the Sequence Listing, as well as having the promoter and enhancer sequences for the expression of the gene ligated thereto. This plasmid was designated pSK-TNP-IgE-H.

2) Light Chain

A pBluescript SK(+) vector was first digested with Sal I and Pst I. Both the Sal I-Pvu II fragment (about 5 kbp) containing promoter [prepared in section (2) above] and the Pvu II-Pst I fragment (about 1.5 kbp) containing the variable region [prepared in section (1) above] were simultaneously ligated into the digested plasmid, using T4 DNA ligase. The resulting plasmid was then digested with Pst I and Not I, and the Pst I-Not I fragment prepared in section (2) above [12 kbp—containing the intron enhancer, the segment coding for the constant region (Cκ) and the 3'-terminal enhancer] was ligated therein using T4 DNA ligase.

The resulting, recombinant plasmid was designated pSK-TNP-IgE-L. This plasmid contains a gene coding for the amino acid sequence as defined by SEQ ID No. 4 in the Sequence Listing (including the leader sequence) as well as the promoter and enhancer sequences for the expression of the gene.

(4) Preparation of Genes to be Introduced

The plasmids pSK-TNP-IgE-H and pSK-TNP-IgE-L, as constructed in (3) above, were linearized by digestion with Sal I and Not I, respectively, and DNA fragments for transfer (heavy chain: about 8.5 kbp; light chain: about 19 kbp) were separated and purified by 0.8% w/v agarose gel electrophoresis. The DNA fragments were further purified by cesium chloride density gradient centrifugation at 75.000 r.p.m. for 16 hours and then dissolved in TE buffer. A mixture of equal amounts of heavy and light chain genes was used for subsequent microinjection.

EXAMPLE 4

Microinjection of DNA

Female mice (BALE/c, 4 weeks old; Nippon SLC, K. K.) were given an ovulation-inducing agent and then placed with male mice of the same strain to mate. On the next day, fertilized eggs in the pronuclear stage were removed from the oviducts of the female mice. About 2 pl of the DNA solution prepared in the section 4 above (1 to 5 µg/ml) were injected into the pronuclei of the fertilized eggs using a glass microcapillary. This procedure was performed according to the literature {"Injection of DNA into fertilized eggs", in Hassei Kogaku Jikken Manual (Developmental engineering experimentation manual), pp.41–76 [Tatsuji Nomura (General ed.), Motoya Katsuki (Ed.), Kodansya, 1987] and "Microinjection of DNA into pronuclei", in Manipulating the Mouse Embryo, A Laboratory Manual, pp.155–173, B. Hogan, F. Costantini and E. Lacy, translated by Kazuya Yamauchi, Yutaka Toyota, Tsuneatsu Mori and Yoichiro Iwakura, Kindai Syuppan, 1989}. The injected, fertilized eggs were transferred to the oviducts of pseudopregnant foster mother mice (Slc:ICR, Nippon SLC, K. K.) and the young were born after about 20 days, either by spontaneous delivery or cesarean section.

EXAMPLE 5

Verification of Gene Transfer (1) Detection of Introduced Genes

1) Synthesis of Primers

PCR was used to determine whether the genes introduced in Example 4 above were retained in the neonates. The following four oligonucleotide primers consisting of the following nucleotide sequences:

5'-GCAAGATGGG GCTTAATCTT TGCTATGG-3'
(sense primer for the heavy chain: SEQ ID No. 5 in the Sequence Listing);
5'-CCACCTTGAT GCTCTAGATA ATTGC-3'
(antisense primer for the heavy chain: SEQ ID No. 6 in the Sequence Listing);
5'-GATGTTTTGA TGACCCAAAC TCCAC-3'
(sense primer for the light chain: SEQ ID No. 7 in the Sequence Listing); and
5'-CTTGGTCCCA GCACCGAACG TGAGC-3'
(antisense primer for the light chain: SEQ ID No. 8 in the Sequence Listing)
were synthesized by the phosphoamidite method.

2) PCR

Genomic DNA was extracted from the tails (about 1 cm in length) of the newborn mice obtained in Example 4 above (3 weeks old), using similar methodology to that described in the Example 2(1) above. The resulting DNA was dissolved in 100 µl of water. Using this DNA as the template, PCR was conducted under the following conditions for each of the heavy and light chains.

Composition of the Reaction Solution:

| | |
|---|---|
| template DNA | 2 µl |
| sense primer (1 µM) | 0.5 µl |
| antisense primer (1 µM) | 0.5 µl |
| 10 × Ex buffer | 2 µl |
| water | 14.5 µl |
| Ex Taq polymerase | 0.5 µl |

Thermal Conditions:

The PCR mix was first heated at 96° C. for 2 minutes, then a cycle of 96° C. for 30 seconds, 50° C. for 1 minute and 72° C. for 1 minute was repeated 30 times, followed by a final incubation at 25° C. for 7 minutes.

After completion of PCR, an aliquot of the reaction solution was taken and subjected to 1.2% w/v agarose gel electrophoresis to confirm the presence or absence of the target band or bands specifically amplified (heavy chain: about 1.5 kbp, light chain: about 300 bp). Three out of the 71 mice from Example 4 were found to harbor genes for both the heavy and the light chains.

The mice that had proven to harbor genes for both of the artificially introduced heavy and light chains were mated with normal BALB/c mice, and the DNA from the offspring was analyzed by the method described above. Approximately 50% of the offspring turned out to retain both of the introduced genes for the heavy and light chains.

(2) Method for Determining IgE Level in Mouse Blood and the Results

Determination of IgE levels in mouse blood was performed by a sandwich ELISA using two anti-mouse IgE antibodies each recognizing a different epitope on the mouse IgE molecule (c.f. Hirano, T. et al. (1988) Int. Archs. Allergy Appl. Immun. 85, 47–54). Sera were taken from mice of over four weeks old for the samples. Mouse IgE (Pharmingen) was used to produce a standard curve.

First, the anti-mouse IgE antibody 6HD5 (5 µg/ml, Yamasa Syoyu, K. K.), diluted with PBS, was dispensed into a 96-well plate for ELISA (Nunc-Immuno Plate, PolySorb Surface; Nunc) at 50 µl/well and kept at 4° C. overnight to optimize adsorption of the antibody on the bottom surface of the wells. After tipping away the antibody solution, 70 µl of a blocking solution [PBS containing 4% w/v bovine serum albumin (BSA, available from Sigma) and 0.2% w/v Tween 20] was added to each well of the plate, which was kept at room temperature for 1 hour for blocking. The blocking solution in the wells was tipped away and the wells were then washed three times with 200 µl/well of a washing solution (PBS containing 0.05% w/v Tween 20). Samples (mouse sera or serial dilutions of standard mouse IgE of a known concentration) diluted with the blocking solution were then added at 50 µl/well and the plate was incubated at 37° C. for 1 hour.

After this time, the samples in the wells were tipped away and the wells were washed three times with 200 µl/well of washing solution. Biotin-labeled anti-mouse IgE HMK12 (5 µg/ml, Yamasa Syoyu, K. K.), diluted with blocking solution, was then added at 50 µl/well and the plate was incubated at 37° C. for 1 hour.

The labeled antibody solution in the wells was then tipped away and the wells were washed three times with 200 µl/well of washing solution. Streptavidin labeled with horseradish peroxidase (Amersham) and diluted 250-fold with blocking solution was then added at 50 µl/well and the plate placed at room temperature for 1 hour.

After this time, the streptavidin solution in the wells was tipped off and the wells were washed three times with 200 µl/well of washing solution. A substrate solution (40 mg/ml o-phenylene diamine, 0.00001% v/v hydrogen peroxide, 40 mM disodium hydrogen phosphate, 50 mM citric acid) was then added at 50 µl/well and the plate placed at room temperature for 20 minutes. At the end of this time, the peroxidase reaction was stopped by the addition of 50 µl/well of 6 N sulfuric acid and the absorbance at 490 nm was determined for each well. The measurements were compared with the standard curve of mouse IgE to determine the IgE concentrations in the samples.

All mice for which the presence of the introduced gene was confirmed showed high blood IgE levels of 8 µg/ml or greater.

(3) Method for Determining Anti-TNP IgE and the Results

The antigen specificity of IgE in the blood of the mice produced in Example 4 above was evaluated by ELISA. First, 50 µl/well of a 5 µg/ml solution of chicken ovalbumin (OVA), either unlabeled or labeled with TNP, was added to an ELISA 96-well plate (Nunc-Immuno Plate, PolySorb Surface: Nunc) and the plate was incubated at 4° C. overnight to optimize adsorption of OVA on the bottom surface of the wells. The OVA-immobilized plate was used to measure TNP specific IgE concentrations by a procedure similar to that described in the preceding section (2). Anti-TNP IgE produced by the hybridoma IGEL-b4 was used for the production of a standard curve.

IgE in the blood of all mice for which the presence of the introduced gene was confirmed bound to TNP-labeled OVA but not to unlabeled OVA, demonstrating that the gene product expressed in the mice was retaining specificity to TNP. Further, from the comparison of anti-TNP IgE concentration in the blood and the IgE concentration determined in section (2) above, it was demonstrated that most of the blood IgE in these mice was the product of the transgene.

TEST EXAMPLES

Test Example 1

Picryl chloride having TNP as a hapten was applied to the ears of unsensitised normal mice and the transgenic mice (those mice produced in Example 4, or their offspring, which were confirmed to possess both introduced genes). No obvious changes were observed for the normal mice, whereas for the transgenic mice, remarkable transient swelling of the skin was observed, with a peak at 1 hour post application. As a control, when a different hapten antigen, oxazolone, was applied, swelling of the ear skin was observed for neither set of mice. Thus, it was confirmed that, for the transgenic mice, no sensitization was required in advance and that, after administering the antigen only once, an antigen specific typical type I allergic reaction could be induced.

Test Example 2

TNP bound to albumin was injected into the tail vein of both normal and transgenic mice, together with "Evans blue" dye. The transgenic mice showed typical symptoms of systemic anaphylaxis such as dyspnea, decrease in body temperature, loss of motions, and extravasation of the blue dye. No such symptoms were observed in the transgenic mice, however, when albumin with no bound TNP was injected. In normal mice, anaphylactic symptoms were not observed in either case.

Test Example 3

Test Methods for Searching for or Verifying the Effectiveness of Anti-allergic Agents In each of the following experimental systems, the effects by pre-administration, co-administration, post-administration or serial administration of a test substance are examined.

(a) Whether a test substance is capable of inhibiting a dermal allergic reaction (swelling of the skin) induced in a transgenic animal of the present invention, such as by the method of Test Example 1 above, may be evaluated by measuring the thickness of the skin.

(b) Whether a test substance is capable of inhibiting systemic anaphylactic shock induced in a transgenic animal of the present invention, such as by the method of Test Example 2 above, may be evaluated by indices such as body temperature, airway resistance and extravasation of dye.

(c) An allergic reaction in the respiratory system can be induced typically by inhalation of an allergen into the transgenic animal of the present invention via the nose or mouth using a nebuliser, for example. Any inhibitory effect of a test substance on an allergic reaction in the respiratory system may be evaluated by measuring airway resistance, compliance of the lung and so on.

(d) An allergic reaction in the digestive system can be induced typically by oral administration of an allergen to the transgenic animal of the present invention. Any inhibitory effect of a test substance on an allergic reaction in the digestive system may be evaluated by, for example, observing mitigation of symptoms such as diarrhea and vomiting.

---

SEQUENCE LISTING

<160> NUMBER OF SEQ ID NOS: 12

<210> SEQ ID NO 1
<211> LENGTH: 1683
<212> TYPE: DNA
<213> ORGANISM: Artificial Sequence
<220> FEATURE:
<223> OTHER INFORMATION: Description of Artificial Sequence: Designed
      DNA encoding the heavy chain of a mouse immunoglobulin E
<220> FEATURE:
<221> NAME/KEY: CDS
<222> LOCATION: (1)..(1683)
<220> FEATURE:
<221> NAME/KEY: sig_peptide
<222> LOCATION: (1)..(57)
<220> FEATURE:
<221> NAME/KEY: mat_peptide
<222> LOCATION: (58)..(1683)

<400> SEQUENCE: 1

```
atg gaa ttg atc tgg gtc ttt ctc ttc ctc ctg tca gta act gca ggt      48
Met Glu Leu Ile Trp Val Phe Leu Phe Leu Leu Ser Val Thr Ala Gly
            -15                 -10                 -5 gtc cac tct gag gtc cag ctt cag cag tct gga gct gag ctg gtg agg      96
Val His Ser Glu Val Gln Leu Gln Gln Ser Gly Ala Glu Leu Val Arg
        -1   1               5                  10 cct ggg tcc tca gtg aag atg tcc tgc aag agt tct gga tat aca ttc     144
Pro Gly Ser Ser Val Lys Met Ser Cys Lys Ser Ser Gly Tyr Thr Phe
    15                  20                  25 aca agc tac ggt ata aac tgg gtg aag cag agg cct gga cag ggc ctg     192
Thr Ser Tyr Gly Ile Asn Trp Val Lys Gln Arg Pro Gly Gln Gly Leu
 30                  35                  40                  45 gaa tgg att gga tat att tat att gga tat ggt tat att gag tat aat     240
Glu Trp Ile Gly Tyr Ile Tyr Ile Gly Tyr Gly Tyr Ile Glu Tyr Asn
```

-continued

```
                      50                        55                        60
gag aag ttc aag ggc aag gcc aca ctg act tca gac aca tcc tcc agg         288
Glu Lys Phe Lys Gly Lys Ala Thr Leu Thr Ser Asp Thr Ser Ser Arg
                      65                        70                        75 aca gcc tac atg caa ctc agc agc ctg aca tct gag gac tct gca atc         336
Thr Ala Tyr Met Gln Leu Ser Ser Leu Thr Ser Glu Asp Ser Ala Ile
                80                        85                        90 tat ttc tgt gca aga tgg ggc tta atc ttt gct atg gac tac tgg ggt         384
Tyr Phe Cys Ala Arg Trp Gly Leu Ile Phe Ala Met Asp Tyr Trp Gly
        95                       100                       105 caa gga acc tca gtc acc gtc tcc tca gcc tct atc agg aac cct cag         432
Gln Gly Thr Ser Val Thr Val Ser Ser Ala Ser Ile Arg Asn Pro Gln
110                      115                       120                       125 ctc tac ccc tta aag ccc tgt aaa ggc act gct tcc atg acc cta ggc         480
Leu Tyr Pro Leu Lys Pro Cys Lys Gly Thr Ala Ser Met Thr Leu Gly
                  130                       135                       140 tgc cta gta aag gac tac ttc cct aat cct gtg act gtg acc tgg tat         528
Cys Leu Val Lys Asp Tyr Phe Pro Asn Pro Val Thr Val Thr Trp Tyr
              145                       150                       155 tca gac tcc ctg aac atg agc act gtg aac ttc cct gcc ctc ggt tct         576
Ser Asp Ser Leu Asn Met Ser Thr Val Asn Phe Pro Ala Leu Gly Ser
              160                       165                       170 gaa ctc aag gtc acc acc agc caa gtg acc agc tgg ggc aag tca gcc         624
Glu Leu Lys Val Thr Thr Ser Gln Val Thr Ser Trp Gly Lys Ser Ala
175                       180                       185 aag aac ttc aca tgc cac gtg aca cat cct cca tca ttc aac gaa agt         672
Lys Asn Phe Thr Cys His Val Thr His Pro Pro Ser Phe Asn Glu Ser
190                       195                       200                       205 agg act atc cta gtt cga cct gtc aca cat tca ctg agc cca cct tgg         720
Arg Thr Ile Leu Val Arg Pro Val Thr His Ser Leu Ser Pro Pro Trp
                  210                       215                       220 agc tac tcc att cat cgc tgc gac ccc aat gca ttc cat tcc acc atc         768
Ser Tyr Ser Ile His Arg Cys Asp Pro Asn Ala Phe His Ser Thr Ile
              225                       230                       235 cag ctg tac tgc ttc att tat ggc cac atc cta aat gat gtc tcc gtc         816
Gln Leu Tyr Cys Phe Ile Tyr Gly His Ile Leu Asn Asp Val Ser Val
          240                       245                       250 agc tgg cta atg gac gat cgg gag ata act gat aca ctt gca caa act         864
Ser Trp Leu Met Asp Asp Arg Glu Ile Thr Asp Thr Leu Ala Gln Thr
      255                       260                       265 gtt cta atc aag gag gaa ggc aaa cta gcc tct acc tgc agt aaa ctc         912
Val Leu Ile Lys Glu Glu Gly Lys Leu Ala Ser Thr Cys Ser Lys Leu
270                       275                       280                       285 aac atc act gag cag caa tgg atg tct gaa agc acc ttc acc tgc agg         960
Asn Ile Thr Glu Gln Gln Trp Met Ser Glu Ser Thr Phe Thr Cys Arg
                  290                       295                       300 gtc acc tcc caa ggc gta gac tat ttg gcc cac act cgg aga tgc cca        1008
Val Thr Ser Gln Gly Val Asp Tyr Leu Ala His Thr Arg Arg Cys Pro
              305                       310                       315 gat cat gag cca cgg ggc gcg att acc tac ctg atc cca ccc agc ccc        1056
Asp His Glu Pro Arg Gly Ala Ile Thr Tyr Leu Ile Pro Pro Ser Pro
              320                       325                       330 ctg gac ctg tat caa aac ggt gct ccc aag ctt acc tgt ctg gtg gtg        1104
Leu Asp Leu Tyr Gln Asn Gly Ala Pro Lys Leu Thr Cys Leu Val Val
          335                       340                       345 gac ctg gaa agc gag aag aat gtc aat gtg acc tgg aac caa gag aag        1152
Asp Leu Glu Ser Glu Lys Asn Val Asn Val Thr Trp Asn Gln Glu Lys
350                       355                       360                       365 aag act tca gtc tca gca tcc cag tgg tac act aag cac cac aat aac        1200
```

```
Lys Thr Ser Val Ser Ala Ser Gln Trp Tyr Thr Lys His His Asn Asn
                370                 375                 380 gcc aca act agt atc acc tcc atc ctg cct gta gtt gcc aag gac tgg      1248
Ala Thr Thr Ser Ile Thr Ser Ile Leu Pro Val Val Ala Lys Asp Trp
            385                 390                 395 att gaa ggc tac ggc tat cag tgc gta gtg gac cgc cct gat ttt ccc      1296
Ile Glu Gly Tyr Gly Tyr Gln Cys Val Val Asp Arg Pro Asp Phe Pro
        400                 405                 410 aag ccc att gtg cgt tcc atc acc ctt ccc cag gtg agc cag cgc tca      1344
Lys Pro Ile Val Arg Ser Ile Thr Leu Pro Gln Val Ser Gln Arg Ser
    415                 420                 425 gcc ccc gag gta tat gtg ttc cca cca cca gag gag gag agc gag gac      1392
Ala Pro Glu Val Tyr Val Phe Pro Pro Pro Glu Glu Glu Ser Glu Asp
430                 435                 440                 445 aaa cgc aca ctc acc tgt ttg atc cag aac ttc ttc cct gag gat atc      1440
Lys Arg Thr Leu Thr Cys Leu Ile Gln Asn Phe Phe Pro Glu Asp Ile
                450                 455                 460 tct gtg cag tgg ctg ggg gat ggc aaa ctg atc tca aac agc cag cac      1488
Ser Val Gln Trp Leu Gly Asp Gly Lys Leu Ile Ser Asn Ser Gln His
            465                 470                 475 agt acc aca aca ccc ctg aaa tcc aat ggc tcc aat caa ggc ttc ttc      1536
Ser Thr Thr Thr Pro Leu Lys Ser Asn Gly Ser Asn Gln Gly Phe Phe
        480                 485                 490 atc ttc agt cgc cta gag gtc gcc aag aca ctc tgg aca cag aga aaa      1584
Ile Phe Ser Arg Leu Glu Val Ala Lys Thr Leu Trp Thr Gln Arg Lys
    495                 500                 505 cag ttc acc tgc caa gtg atc cat gag gca ctt cag aaa ccc agg aaa      1632
Gln Phe Thr Cys Gln Val Ile His Glu Ala Leu Gln Lys Pro Arg Lys
510                 515                 520                 525 ctg gag aaa aca ata tcc aca agc ctt ggt aac acc tcc ctc cgt ccc      1680
Leu Glu Lys Thr Ile Ser Thr Ser Leu Gly Asn Thr Ser Leu Arg Pro
                530                 535                 540 tcc                                                                   1683
Ser

<210> SEQ ID NO 2
<211> LENGTH: 561
<212> TYPE: PRT
<213> ORGANISM: Artificial Sequence
<220> FEATURE: Description of Artificial Sequence: Designed heavy
      chain of a mouse immunoglobulin E

<400> SEQUENCE: 2

Met Glu Leu Ile Trp Val Phe Leu Phe Leu Leu Ser Val Thr Ala Gly
                -15                 -10                  -5

Val His Ser Glu Val Gln Leu Gln Gln Ser Gly Ala Glu Leu Val Arg
         -1   1               5                  10

Pro Gly Ser Ser Val Lys Met Ser Cys Lys Ser Gly Tyr Thr Phe
     15                  20                  25

Thr Ser Tyr Gly Ile Asn Trp Val Lys Gln Arg Pro Gly Gln Gly Leu
 30                  35                  40                  45

Glu Trp Ile Gly Tyr Ile Tyr Ile Gly Tyr Gly Tyr Ile Glu Tyr Asn
                 50                  55                  60

Glu Lys Phe Lys Gly Lys Ala Thr Leu Thr Ser Asp Thr Ser Ser Arg
             65                  70                  75

Thr Ala Tyr Met Gln Leu Ser Ser Leu Thr Ser Glu Asp Ser Ala Ile
         80                  85                  90

Tyr Phe Cys Ala Arg Trp Gly Leu Ile Phe Ala Met Asp Tyr Trp Gly
     95                 100                 105
```

```
Gln Gly Thr Ser Val Thr Val Ser Ser Ala Ser Ile Arg Asn Pro Gln
110                 115                 120                 125

Leu Tyr Pro Leu Lys Pro Cys Lys Gly Thr Ala Ser Met Thr Leu Gly
                130                 135                 140

Cys Leu Val Lys Asp Tyr Phe Pro Asn Pro Val Thr Val Thr Trp Tyr
            145                 150                 155

Ser Asp Ser Leu Asn Met Ser Thr Val Asn Phe Pro Ala Leu Gly Ser
        160                 165                 170

Glu Leu Lys Val Thr Thr Ser Gln Val Thr Ser Trp Gly Lys Ser Ala
    175                 180                 185

Lys Asn Phe Thr Cys His Val Thr His Pro Pro Ser Phe Asn Glu Ser
190                 195                 200                 205

Arg Thr Ile Leu Val Arg Pro Val Thr His Ser Leu Ser Pro Pro Trp
                210                 215                 220

Ser Tyr Ser Ile His Arg Cys Asp Pro Asn Ala Phe His Ser Thr Ile
                225                 230                 235

Gln Leu Tyr Cys Phe Ile Tyr Gly His Ile Leu Asn Asp Val Ser Val
            240                 245                 250

Ser Trp Leu Met Asp Asp Arg Glu Ile Thr Asp Thr Leu Ala Gln Thr
    255                 260                 265

Val Leu Ile Lys Glu Glu Gly Lys Leu Ala Ser Thr Cys Ser Lys Leu
270                 275                 280                 285

Asn Ile Thr Glu Gln Gln Trp Met Ser Glu Ser Thr Phe Thr Cys Arg
                290                 295                 300

Val Thr Ser Gln Gly Val Asp Tyr Leu Ala His Thr Arg Arg Cys Pro
            305                 310                 315

Asp His Glu Pro Arg Gly Ala Ile Thr Tyr Leu Ile Pro Pro Ser Pro
        320                 325                 330

Leu Asp Leu Tyr Gln Asn Gly Ala Pro Lys Leu Thr Cys Leu Val Val
    335                 340                 345

Asp Leu Glu Ser Glu Lys Asn Val Asn Val Thr Trp Asn Gln Glu Lys
350                 355                 360                 365

Lys Thr Ser Val Ser Ala Ser Gln Trp Tyr Thr Lys His His Asn Asn
                370                 375                 380

Ala Thr Thr Ser Ile Thr Ser Ile Leu Pro Val Val Ala Lys Asp Trp
            385                 390                 395

Ile Glu Gly Tyr Gly Tyr Gln Cys Val Val Asp Arg Pro Asp Phe Pro
        400                 405                 410

Lys Pro Ile Val Arg Ser Ile Thr Leu Pro Gln Val Ser Gln Arg Ser
    415                 420                 425

Ala Pro Glu Val Tyr Val Phe Pro Pro Glu Glu Glu Ser Glu Asp
430                 435                 440                 445

Lys Arg Thr Leu Thr Cys Leu Ile Gln Asn Phe Phe Pro Glu Asp Ile
                450                 455                 460

Ser Val Gln Trp Leu Gly Asp Gly Lys Leu Ile Ser Asn Ser Gln His
            465                 470                 475

Ser Thr Thr Thr Pro Leu Lys Ser Asn Gly Ser Asn Gln Gly Phe Phe
        480                 485                 490

Ile Phe Ser Arg Leu Glu Val Ala Lys Thr Leu Trp Thr Gln Arg Lys
    495                 500                 505

Gln Phe Thr Cys Gln Val Ile His Glu Ala Leu Gln Lys Pro Arg Lys
510                 515                 520                 525
```

```
Leu Glu Lys Thr Ile Ser Thr Ser Leu Gly Asn Thr Ser Leu Arg Pro
                530                 535                 540

Ser

<210> SEQ ID NO 3
<211> LENGTH: 714
<212> TYPE: DNA
<213> ORGANISM: Artificial Sequence
<220> FEATURE:
<223> OTHER INFORMATION: Description of Artificial Sequence: Designed
      DNA encoding the light chain of a mouse immunoglobulin E
<220> FEATURE:
<221> NAME/KEY: CDS
<222> LOCATION: (1)..(714)
<220> FEATURE:
<221> NAME/KEY: sig_peptide
<222> LOCATION: (1)..(57)
<220> FEATURE:
<221> NAME/KEY: mat_peptide
<222> LOCATION: (58)..(714)

<400> SEQUENCE: 3 atg aag ttg cct gtt agg ctg ttg gtg ctg atg ttc tgg att cct gct      48
Met Lys Leu Pro Val Arg Leu Leu Val Leu Met Phe Trp Ile Pro Ala
            -15                 -10                 -5 tcc agc agt gat gtt ttg atg acc caa act cca ctc tcc ctg cct gtc     96
Ser Ser Ser Asp Val Leu Met Thr Gln Thr Pro Leu Ser Leu Pro Val
        -1  1               5                  10 agt ctt gga gat caa gcc tcc atc tct tgc aga tct agt cag agc att    144
Ser Leu Gly Asp Gln Ala Ser Ile Ser Cys Arg Ser Ser Gln Ser Ile
        15                  20                  25 gta cat agt aat gga aac acc tat tta gaa tgg tac ctg cag aaa cca    192
Val His Ser Asn Gly Asn Thr Tyr Leu Glu Trp Tyr Leu Gln Lys Pro
 30                  35                  40                  45 ggc cag tct cca aag ctc ctg atc tac aaa gtt tcc aac cga ttt tct    240
Gly Gln Ser Pro Lys Leu Leu Ile Tyr Lys Val Ser Asn Arg Phe Ser
                 50                  55                  60 ggg gtc cca gac agg ttc agt ggc agt gga tca ggg aca gat ttc aca    288
Gly Val Pro Asp Arg Phe Ser Gly Ser Gly Ser Gly Thr Asp Phe Thr
             65                  70                  75 ctc aag atc agc aga gtg gag gct gag gat ctg gga gtt tat tac tgc    336
Leu Lys Ile Ser Arg Val Glu Ala Glu Asp Leu Gly Val Tyr Tyr Cys
         80                  85                  90 ttt caa ggt tca cat gtt ccg ctc acg ttc ggt gct ggg acc aag ctg    384
Phe Gln Gly Ser His Val Pro Leu Thr Phe Gly Ala Gly Thr Lys Leu
     95                 100                 105 gag ctg aaa cgg gct gat gct gca cca act gta tcc atc ttc cca cca    432
Glu Leu Lys Arg Ala Asp Ala Ala Pro Thr Val Ser Ile Phe Pro Pro
110                 115                 120                 125 tcc agt gag cag tta aca tct gga ggt gcc tca gtc gtg tgc ttc ttg    480
Ser Ser Glu Gln Leu Thr Ser Gly Gly Ala Ser Val Val Cys Phe Leu
                130                 135                 140 aac aac ttc tac ccc aaa gac atc aat gtc aag tgg aag att gat ggc    528
Asn Asn Phe Tyr Pro Lys Asp Ile Asn Val Lys Trp Lys Ile Asp Gly
            145                 150                 155 agt gaa cga caa aat ggc gtc ctg aac agt tgg act gat cag gac agc    576
Ser Glu Arg Gln Asn Gly Val Leu Asn Ser Trp Thr Asp Gln Asp Ser
        160                 165                 170 aaa gac agc acc tac agc atg agc agc acc ctc acg ttg acc aag gac    624
Lys Asp Ser Thr Tyr Ser Met Ser Ser Thr Leu Thr Leu Thr Lys Asp
    175                 180                 185 gag tat gaa cga cat aac agc tat acc tgt gag gcc act cac aag aca    672
Glu Tyr Glu Arg His Asn Ser Tyr Thr Cys Glu Ala Thr His Lys Thr
```

```
                190                 195                 200                 205
tca act tca ccc att gtc aag agc ttc aac agg aat gag tgt                              714
Ser Thr Ser Pro Ile Val Lys Ser Phe Asn Arg Asn Glu Cys
                210                 215
```

<210> SEQ ID NO 4
<211> LENGTH: 238
<212> TYPE: PRT
<213> ORGANISM: Artificial Sequence
<220> FEATURE: Description of Artificial Sequence: Designed heavy
      chain of a mouse immunoglobulin E

<400> SEQUENCE: 4

```
Met Lys Leu Pro Val Arg Leu Leu Val Leu Met Phe Trp Ile Pro Ala
            -15                 -10                  -5

Ser Ser Ser Asp Val Leu Met Thr Gln Thr Pro Leu Ser Leu Pro Val
         -1   1               5                  10

Ser Leu Gly Asp Gln Ala Ser Ile Ser Cys Arg Ser Ser Gln Ser Ile
         15                  20                  25

Val His Ser Asn Gly Asn Thr Tyr Leu Glu Trp Tyr Leu Gln Lys Pro
 30                  35                  40                  45

Gly Gln Ser Pro Lys Leu Leu Ile Tyr Lys Val Ser Asn Arg Phe Ser
             50                  55                  60

Gly Val Pro Asp Arg Phe Ser Gly Ser Gly Ser Gly Thr Asp Phe Thr
             65                  70                  75

Leu Lys Ile Ser Arg Val Glu Ala Glu Asp Leu Gly Val Tyr Tyr Cys
         80                  85                  90

Phe Gln Gly Ser His Val Pro Leu Thr Phe Gly Ala Gly Thr Lys Leu
     95                 100                 105

Glu Leu Lys Arg Ala Asp Ala Ala Pro Thr Val Ser Ile Phe Pro Pro
110                 115                 120                 125

Ser Ser Glu Gln Leu Thr Ser Gly Gly Ala Ser Val Val Cys Phe Leu
                130                 135                 140

Asn Asn Phe Tyr Pro Lys Asp Ile Asn Val Lys Trp Lys Ile Asp Gly
            145                 150                 155

Ser Glu Arg Gln Asn Gly Val Leu Asn Ser Trp Thr Asp Gln Asp Ser
        160                 165                 170

Lys Asp Ser Thr Tyr Ser Met Ser Ser Thr Leu Thr Leu Thr Lys Asp
    175                 180                 185

Glu Tyr Glu Arg His Asn Ser Tyr Thr Cys Glu Ala Thr His Lys Thr
190                 195                 200                 205

Ser Thr Ser Pro Ile Val Lys Ser Phe Asn Arg Asn Glu Cys
                210                 215
```

<210> SEQ ID NO 5
<211> LENGTH: 28
<212> TYPE: DNA
<213> ORGANISM: Artificial Sequence
<220> FEATURE:
<223> OTHER INFORMATION: Description of Artificial Sequence: PCR primer
      to detect a transgene encoding the heavy chain of immunoglobulin E

<400> SEQUENCE: 5
gcaagatggg gcttaatctt tgctatgg                                                28

<210> SEQ ID NO 6
<211> LENGTH: 25
<212> TYPE: DNA
<213> ORGANISM: Artificial Sequence

```
<220> FEATURE:
<223> OTHER INFORMATION: Description of Artificial Sequence: PCR primer
      to detect a transgene encoding the light chain of immunoglobulin E

<400> SEQUENCE: 6
ccaccttgat gctctagata attgc                                              25

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: PCR primer
      to detect a transgene encoding the heavy chain of immunoglobulin E

<400> SEQUENCE: 7
gatgttttga tgacccaaac tccac                                              25

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: PCR primer
      to detect a transgene encoding the light chain of immunoglobulin E

<400> SEQUENCE: 8
cttggtccca gcaccgaacg tgagc                                              25

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: PCR primer
      to amplify the fragment of a DNA encoding the constant region of
      heavy chain of mouse immunoglobulin E

<400> SEQUENCE: 9
ctcaacatca ctgagcagca atgg                                               24

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence: PCR primer
      to amplify the fragment of a DNA encoding the constant region of
      heavy chain of mouse immunoglobulin E

<400> SEQUENCE: 10
gcgttattgt ggtgcttagt gtacc                                              25

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: PCR primer
      to amplify the enhancer region of mouse immunoglobulin heavy chain
      gene

<400> SEQUENCE: 11
tagaattcat tttcaaaatt agg                                                23

<210> SEQ ID NO 12
<211> LENGTH: 25
```

-continued

```
<212> TYPE: DNA
<213> ORGANISM: Artificial Sequence
<220> FEATURE:
<223> OTHER INFORMATION: Description of Artificial Sequence: PCR primer
      to amplify the enhancer region of mouse immunoglobulin heavy chain
      gene

<400> SEQUENCE: 12
agtctagata attgcattca tttaa                                              25
```

What is claimed is:

1. A transgenic mouse having a genome which has been altered to constitutively express an IgE molecule having an immunoglobulin structure comprising:

an IgE heavy chain variable region and constant region encoded by nucleotides 1 to 1683 of SEQ ID NO: 1 and an IgE light chain variable region and constant region encoded by nucleotides 1 to 714 of SEQ ID NO: 3; and wherein said IgE heavy chain constant region lacks a transmembrane region and said molecule binds IgE receptors on murine mast cells; said molecule having an antigen recognition site having specificity for an antigen having one or more trinitrophenyl groups, resulting in a phenotype selected from the group consisting of epidermal swelling following topical application of said antigen having one or more trinitrophenyl groups, systemic anaphylaxis shock with dyspnea, decrease in body temperature, and loss of motion.

2. The transgenic mouse of claim 1, which is allergic to said antigen without prior sensitization to the antigen.

3. The transgenic mouse of claim 1, which has a blood level of said molecule of at least 8 µg/ml.

4. The transgenic mouse of claim 1, which has a blood level of said molecule at least as high as the blood level of IgE specific for said antigen in a non-transgenic mouse which has been sensitized to said antigen.

5. The transgenic mouse of claim 1, which is homozygous for genes introduced in the genome, said genes being transgenes encoded by the nucleotide sequences of each of SEQ ID NOS: 1 and 3.

6. A process for making a transgenic mouse according to claim 1, said process comprising:

(a) microinjecting linearized fragments of plasmids encoding each of SEQ ID NO: 1 and SEQ ID NO: 3 into a fertilized egg of a mouse, (b) transferring said fertilized egg to the oviduct of a female mouse which has previously been treated to induce pseudopregnancy, and (c) allowing said egg to develop in the uterus of the female mouse.

7. A process for evaluating the anti-allergic activity of a substance against a physiological condition brought on by exposure to a trinitrophenyl group-containing antigen, comprising obtaining the transgenic mouse of claim 1, wherein said molecule is specific for said trinitrophenyl group-containing antigen, and applying the substance to be evaluated to said transgenic mouse.

8. The transgenic mouse of claim 1, wherein the transgenic mouse exhibits a phenotype selected from the group consisting of epidermal swelling following topical application of said antigen, systemic anaphylaxis shock with dyspnea, decrease in body temperature, and loss of motion, after a single administration of the trinitrophenyl group-containing antigen, without the necessity for prior sensitization.

9. A process for determining the effectiveness of a substance to counter an allergic reaction to a trinitrophenyl group-containing antigen comprising administering the substance to the transgenic mouse of claim 1 and evaluating a physical condition of the transgenic mouse as an indication of an anti-allergic effect.

10. The transgenic mouse of claim 1, wherein said genome has been altered using genomic DNA.

11. The transgenic mouse of claim 10, wherein said genomic DNA comprise a murine kappa promoter and enhancer region.

* * * * *

UNITED STATES PATENT AND TRADEMARK OFFICE
CERTIFICATE OF CORRECTION

PATENT NO.   : 6,118,044
DATED        : September 12, 2000
INVENTOR(S)  : Karasuyama et al.

It is certified that error appears in the above-identified patent and that said Letters Patent is hereby corrected as shown below:

<u>Title page, Item [54] and Column 1, line 1,</u>
In the title, delete "ANIMAL" and insert -- MOUSE --.

Signed and Sealed this

Second Day of July, 2002

*Attest:*

JAMES E. ROGAN
*Director of the United States Patent and Trademark Office*

*Attesting Officer*